United States Patent [19]

Vosika et al.

[11] Patent Number: 5,416,070
[45] Date of Patent: * May 16, 1995

[54] COMPOSITION FOR MACROPHAGE ACTIVATION

[75] Inventors: Gerald J. Vosika, Moorhead, Minn.; Dennis A. Cornelius; John A. Bennek, both of Fargo, N. Dak.; Karl E. Swenson, Gahanna, Ohio; Carl W. Gilbert, Fargo, N. Dak.

[73] Assignee: ImmunoTherapeutics, Inc., Fargo, N. Dak.

[*] Notice: The portion of the term of this patent subsequent to Aug. 21, 2007 has been disclaimed.

[21] Appl. No.: 509,338

[22] Filed: Apr. 13, 1990

Related U.S. Application Data

[63] Continuation-in-part of Ser. No. 216,789, Jul. 8, 1988, Pat. No. 4,950,645.

[51] Int. Cl.$^6$ .......................... A61K 37/02; C07K 9/00
[52] U.S. Cl. ............................................. 514/8; 530/322; 424/450; 424/130.1; 424/194.1
[58] Field of Search ........................... 514/8; 530/322; 424/88–92, 450, 130.1–194.1

[56] References Cited

U.S. PATENT DOCUMENTS

| | | | |
|---|---|---|---|
| 3,976,544 | 8/1976 | Adam et al. | 195/2 |
| 4,042,678 | 8/1977 | Ciorbaru et al. | 424/12 |
| 4,094,971 | 6/1978 | Chedid et al. | 424/92 |
| 4,101,536 | 7/1978 | Yamumura et al. | 260/112.5 R |
| 4,153,684 | 5/1979 | Audibert et al. | 24/88 |
| 4,158,052 | 6/1979 | Audibert et al. | 424/45 |
| 4,172,125 | 10/1979 | Audibert et al. | 424/89 |
| 4,185,089 | 1/1980 | Derrien et al. | 424/88 |
| 4,186,194 | 1/1980 | Adam et al. | 424/89 |
| 4,235,771 | 11/1980 | Adam et al. | 260/112.5 R |
| 4,256,735 | 3/1981 | Durette et al. | 424/177 |
| 4,271,151 | 6/1981 | Hotta et al. | 530/322 |
| 4,272,524 | 6/1981 | Chedid et al. | 424/177 |
| 4,317,771 | 3/1982 | Shiba et al. | 424/177 |
| 4,323,559 | 4/1982 | Audibert et al. | 424/177 |
| 4,357,322 | 11/1982 | Rooks, III et al. | 424/177 |
| 4,357,323 | 11/1982 | Soma et al. | 424/180 |
| 4,370,265 | 1/1983 | Adam et al. | 260/112.5 R |
| 4,382,080 | 5/1983 | Shiba et al. | 424/177 |
| 4,391,800 | 7/1983 | Durette et al. | 424/177 |
| 4,395,399 | 7/1983 | Ovchinnikov et al. | 424/177 |
| 4,396,607 | 8/1983 | Lefrancier et al. | 424/177 |
| 4,397,844 | 8/1983 | Baschang et al. | 424/177 |
| 4,401,659 | 8/1983 | Lefrancier et al. | 424/177 |
| 4,406,890 | 9/1983 | Tarcsay et al. | 424/177 |
| 4,414,204 | 11/1983 | Tarcsay et al. | 424/177 |
| 4,427,659 | 1/1984 | Lefrancier et al. | 424/177 |
| 4,435,386 | 3/1984 | Ribi et al. | 424/177 |
| 4,436,727 | 3/1984 | Ribi et al. | 424/177 |
| 4,436,728 | 3/1984 | Ribi et al. | 424/177 |
| 4,446,128 | 5/1984 | Baschang et al. | 424/88 |
| 4,461,761 | 7/1984 | Lefrancier et al. | 424/177 |
| 4,505,899 | 3/1985 | Ribi et al. | 514/8 |
| 4,505,900 | 3/1985 | Ribi et al. | 514/2 |
| 4,515,891 | 5/1985 | Yokogawa et al. | 435/69 |
| 4,522,811 | 6/1985 | Eppstein et al. | 514/2 |
| 4,545,932 | 10/1985 | Takase et al. | 260/112.5 |
| 4,770,874 | 9/1988 | Allison et al. | 524/88 |
| 4,950,645 | 8/1992 | Vosika et al. | 514/8 |

FOREIGN PATENT DOCUMENTS 7504003 of 1975 France.

OTHER PUBLICATIONS

T. Andronova, et al., *Chem. of Pept. and Prot.*, 1, 343 (1982).
D. G. Brown et al., *Immunotoxicology*, A. Belin, et al., (List continued on next page.)

*Primary Examiner*—Jill A. Johnston
*Assistant Examiner*—P. Lynn Touzeau
*Attorney, Agent, or Firm*—Merchant, Gould, Smith, Edell, Welter & Schmidt

[57] ABSTRACT

The present invention provides novel lipophilic disaccharide-dipeptide compounds. The compounds of the invention are preferably encapsulated into multilamellar liposomes, which can be formed from phosphatidyl choline and phosphatidyl glycerol. The compounds are effective in activating human monocytes with subsequent destruction of tumor cells. These compounds have acceptable toxicity in anticipated human dosages.

33 Claims, No Drawings

OTHER PUBLICATIONS

Ed; Martin Hijhof, Pub.; 1987, pp. 219–233 *Eur. J. Biochem.*, 143, 359 (1984).
M. Guinand, et al., *Eur. J. Biochem.*, 143, 359 (1984).
W. R. Hargreaves, et al., *Biochem.*, 17, 3759 (1978).
V. T. Ivanov, et al., "Synthesis, Structure and Biological Properties of Glycopeptides Containing the N-Acetyl-Glucosaminyl-O-(1-4)-N-Acetylmuramyl Disaccharide Unit", Proceedings of the Sixteen European Peptide Symposium, Brunfeldt K. ed., Striptor Copenhagen, 1991, pp. 494–500.
N. C. Phillips, et al., *Cancer Res.*, 45, 128 (1985).
S. Sone, et al., *Cancer Immunol. Immunother.*, 12, 203 (1982).
E. Ribi, et al., *Ann. N.Y. Acad. Science, U.S.A.*, 277, 228 (1976).
G. Sava, et al., *Cancer Immunol. Immunother.*, 18, 49 (1984).
G. Sava, et al., *Cancer Immunol. Immunother.*, 15, 84 (1983).
*Biological Abstracts*, vol. 89, 1990 (Philadelphia, Pa., US) J. G. Vosika et al.: "Immunologic and Toxicologic Study of Disaccharide Tripeptide Glycerol Dipalmitoyl: A New Lipophilic Immunomodulator" (see p. 779, abstract No. 118879 & Mol Boiter 2(1): 50–56 1990.

COMPOSITION FOR MACROPHAGE ACTIVATION

This application is a continuation-in-part of Application Ser. No. 07/216,789, filed Jul. 8, 1988, now U.S. Pat. No. 4,950,645, issued Aug. 21, 1990.

FIELD OF THE INVENTION

The present invention provides novel lipophilic disaccharide-tripeptide compounds having improved immunological efficacy, and a liposome encapsulated composition comprising said compounds.

BACKGROUND OF THE INVENTION

Intact microbial agents are known to have immunological effects. These effects include both immunoadjuvant efficacy and antitumor effects, in both experimentally induced and human malignancies. The active components, consisting of the peptidoglycan cell wall skeleton and trehalose dimycolate, have been isolated from mycobacteria. These active components, especially when attached to mineral oil or squalene, are known to be as active as the intact microbial agents. See, for example, E. Ribi et al., *Ann. NY Acad. Science U.S.A.*, 277, 228–236 (1976).

The cell wall skeleton of *Nocardia rubra* (N-CWS) is also known to activate macrophages. Given intravenously, oil-attached N-CWS can cure some rats with experimental pulmonary metastases. See, for example, S. Sone et al., *Cancer Immunology Immunotherapy*, 12, 203–209 (1982). Smaller, water soluble monomeric units of the cell wall peptidoglycans have been demonstrated to be adjuvant active. Adjuvants are compounds causing stimulation of the immune system of a human or other mammal which result in an increased production of antibodies and in an enhancement of the protective reaction of the organism, e.g., against infection. Such monomeric units have also shown antitumor activity when given intravenously, for example, in mice bearing the Lewis lung carcinoma or the MCA mammary carcinoma. See, for example, G. Sava et al., *Cancer Immunology Immunotherapy*, 15, 84–86 (1983).

The active components of these organisms have been isolated, purified, and synthesized. These components are glycopeptides constituting a broad class of organic compounds which include a sugar part and a peptide part. Glycopeptides found in the cell are known to retain not only adjuvant activity, as evidenced by their ability to increase the antibody response, but also possess antitumor activity, as evidenced by their ability to activate macrophages to become cytotoxic and destroy tumor cells. For example, muramyl dipeptide (MDP) (e.g., N-acetylmuramyl-L-alanyl-D-isoglutamine) and a large number of MDP derivatives are known to have antitumor macrophage activation properties.

Both the in vitro and in vivo antitumor activity of mono- and disaccharide peptides is increased by their incorporation into liposomes. Lipophilic derivatives of immunomodulators and/or antitumor agents are known. Such compounds are useful for efficiently incorporating these agents into liposomes for targeting macrophages and activating macrophages to the cytotoxic state.

Both the intact microbial agents and many MDP analogues have shown an undesirable level of toxicity. Intact microbial agents, used alone or in an oil-water emulsion, such as Freund's adjuvant, can cause an increased sensitivity to histamine, granuloma formation, and hyperplasia of the liver and spleen. In particular, the administration of N-acetylmuramyl-L-alanyl-D-isoglutaminyl-L-alanyl-phosphatidylethanolamine, when given in repeated doses, has caused the undesirable toxic reaction of generalized vasculitis (See, D. G. Brown el al. in *Immunotoxicology*, A. Belin et al., Ed; Martin Hijhof, Pub.; 1987, pp. 219–233).

Therefore, there is a need for novel glycopeptide compounds which have improved adjuvant and/or antitumor activity, which are readily incorporated into liposomes, and which have acceptable toxicity in dosages exceeding anticipated effective human dosages.

SUMMARY OF THE INVENTION

The present invention provides novel lipophilic disaccharide-tripeptide compounds. The compound of the invention is preferably encapsulated into multilamellar liposomes, which can be formed from, for example, phosphatidyl choline and phosphatidyl glycerol. The compounds are effective in activating human monocytes. These compounds have acceptable levels of toxicity in dosages exceeding anticipated human dosages.

The compound of the invention has the formula (I):

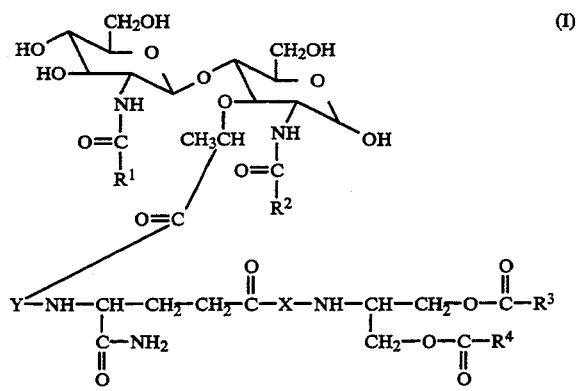

or the formula (II):

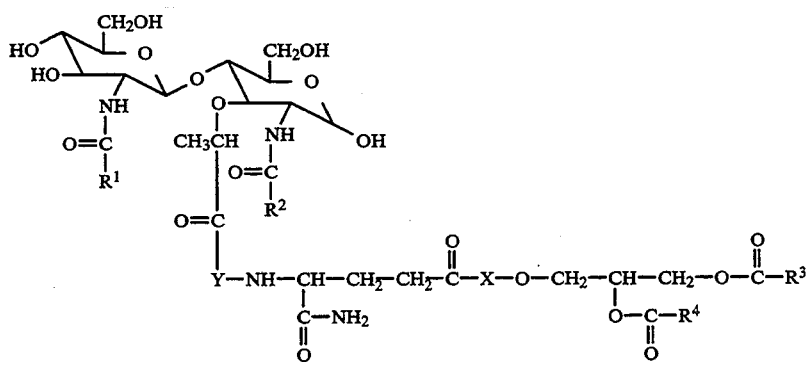

(II)

wherein R¹ is a (C₁–C₉)alkyl group, R² is a (C₁–C₅)alkyl group, R³ and R⁴ are individually (C₆–C₃₀)alkyl groups having about 0–4 double bonds.

X is a spacer group that does not substantially adversely affect the activity or toxicity of the compound. X is particularly a single bond, or any peptidyl residue comprising one or more amino acids. X is preferably any amino acid residue of the general formula:

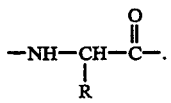

More preferably X is any naturally occurring amino acid residue or an enantiomorph of any naturally occurring amino acid residue. Particularly useful compounds of the present invention include an X group selected from the group consisting of neutral naturally occurring amino acid residues, and more particularly neutral aliphatic naturally occurring amino acids, and the enantiomorphs of these amino acid residues. L, D, or DL mixtures of valine and alanine, are particularly preferred.

Y is any amino acid residue of the general formula:

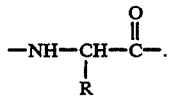

Preferably Y is any naturally occurring amino acid residue or an enantiomorph of any naturally occurring amino acid residue. Particularly useful compounds of the present invention include a Y group selected from the group consisting of neutral naturally occurring amino acid residues, and more particularly neutral aliphatic naturally occurring amino acids, and the enantiomorphs of these amino acid residues. L, D, or DL mixtures of threonine, alanine, valine, and serine are particularly preferred. L-threonine and L-alanine are most preferred.

The pharmaceutically acceptable salts of the compounds, and a liposome comprising a compound of the above formulas, are also within the scope of the invention. In addition to the L-enantiomorphs and the D-enantiomorphs, DL-mixtures of amino acids can also be used in the present compositions.

DETAILED DESCRIPTION OF THE INVENTION

Chemical Structure of Compounds I and II

The compounds of the present invention (Compounds I and II) are novel lipophilic disaccharide-tripeptides. Compounds I and II include a glucosamine (Glc) derivative having an acyl group with about 2 to 10 carbons attached to the nitrogen. Preferably, the acyl group has 2 carbons (acetyl) forming N-acetylglucosamine (GlcNAc).

The N-acylglucosamine moiety is attached to an N-acylmuramyl moiety. The acyl functionality attached to the nitrogen of the muramyl group has about 2 to 6 carbons, preferably 2 carbons, forming an N-acetylmuramyl group (MurNAc). The alternating disaccharide GlcNAc-MurNAc is a naturally occurring disaccharide, found in bacterial cell walls as part of a polymeric glycopeptide. See, U.S. Pat. No. 4,395,399.

The disaccharide moiety of Compounds I and II, N-acylglucosamine-N-acylmuramate, is bonded to the N-terminus of a peptidyl moiety, Y, through the lactyl ether linkage at the number 3 position on the muramyl group. The amino acid residue, Y, is bonded to D-isoglutamine (isoGln), which is bonded through the C-terminus to the group, X.

Neutral naturally occurring amino acid residues for use in the X and Y positions are of particular interest. Neutral naturally occurring amino acids include neutral aliphatic, neutral thioaliphatic, neutral aromatic, and neutral heterocyclic amino acids. Neutral aliphatic naturally occurring amino acids include: glycine (Gly), alanine (Ala), serine (Ser), threonine (Thr), valine (Val), leucine (Leu), and isoleucine (Ile). Neutral thioaliphatic amino acids include: cysteine (Cys), cystine (CyS-Cys), and methionine (Met). Neutral aromatic amino acids include phenylalanine (Phe) and tyrosine (Tyr). Neutral heterocyclic amino acids include: proline (Pro), hydroxyproline (Hyp), and tryptophan (Trp). Other naturally occurring amino acids, include: the acidic amino acids aspartic acid (Asp) and glutamic acid (Glu); and the basic amino acids, histidine (His), lysine (Lys) and arginine (Arg).

Preferred peptidyl moieties include L-alanyl-D-isoglutaminyl-L-alanine (L-Ala-D-isoGln-L-Ala); L-alanyl-D-isoglutaminyl-D-alanine (L-Ala-D-isoGln-D-Ala); and D-alanyl-D-isoglutaminyl-D-alanine (D-Ala-D-isoGln-D-Ala). The disaccharide-tripeptide portion of the novel compound may be referred to as N-acylglucosaminyl-N-acylmuramyltripeptide.

Compounds I and II differ at the lipophilic end of the compounds. The lipophilic end of the compounds of the invention comprise a derivative of glycerol substituted with two acyl groups, the acyl groups individually having between 7 and 31 carbons, preferably between 13 and 24 carbons (i.e., R³ and R⁴ are individually (C₁₂–C₂₃)alkyl groups), and about 0 to 4 double bonds, preferably about 0 to 1 double bond. Preferably both acyl groups have 16 carbons [$C_{16}$] (i.e., $R^3$ and $R^4$ are individually ($C_{15}$)alkyl groups) to form a dipalmitoyl-glycerol (DPG) derivative. In Compound I the glycerol derivative is attached to the C-terminus of the terminal amino acid of X, through an amide linkage:

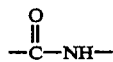

attached to the number two carbon of the glycerol backbone. In Compound II the glycerol derivative is attached to the C-terminus of the terminal amino acid of X, through an ester linkage

attached to the number three carbon of the glycerol (sn) backbone.

Novel compounds of the present invention can generally be described as N-acylglucosaminyl-N-acyl-muramyltripeptide-diacyl-glycerol compounds. Preferred compounds are GlcNAcMurNAc-L-Ala-D-isoGln-L-Ala-DpG; GlcNAcMurNAc-L-Ala-D̄-isoGln-D̄-Ala-DpG; GlcNAcMurNAc-D̄-Ala-D̄-isoGln-D̄-Ala-DPG; GlcNAcMurNAc-L-Ala-D̄-isoGln-L̄-Ala-NHDPG; GlcNAcMurNAc-L-Ala-D̄-isoGln-D̄-Ala-NHDPG; and GlcNAcMurNAc-D-Ala-D-isoGln-D-Ala-NHDPG.

Compounds I and II may also be used as the pharmaceutically acceptable salts of the formulas above. Such salts include the amine salts which are derived from the epsilon amino groups of lysine and the organic acids such as citrate, lactic, malic, methane sulfonic, p-toluene sulfonic, and the like; as well as inorganic acids such as hydrochloric acid, sulfuric acid, phosphoric acid, and the like. Salts such as (lower) alkyl sulfate and halides can also be used. If X or Y have a free carboxyl side chain, such as with aspartic or glutamic acid, such salts could include those derived from inorganic bases such as KOH, NaOH, and the like, from NH4OH, or from organic amines. For isolation or purification of the compound, pharmaceutically unacceptable salts may also be used. However, only the pharmaceutically acceptable, nontoxic salts can be used therapeutically, and are therefore preferred.

Liposomes

The liposomes are generally produced from phospholipids or other lipid substances and are formed of mono- or multilamellar hydrated liquid crystals. They are customarily used in dispersions in an aqueous carrier medium. The use of liposomes incorporating Compounds I and II results in an increase in the adjuvant and anti-tumor activity. Also, an increase in humoral and/or cellular mediation immune responses is often observed. Thus, Compounds I and II are preferably included in liposomes.

There are a number of conventional procedures to form liposomes. Any nontoxic, physiologically acceptable and metabolizable lipid, capable of forming liposomes, can be used. The most usual lipids are the phospholipids, and notably the phosphatidyl cholines (lecithins), both natural and synthetic. Phospholipids may also be used, for example, the phosphatidyl serines, the phosphatidyl inositides, or the sphingomyelines. Other lipids can also be used, which have been described, for example, by W. R. Hargreaves and D. W. Deamer (Conference on Liposomes and Their Uses in Biology and Medicine, Sep. 14–16, 1977, *New York Acad. Sci.*) and in *Biochem.*, 18, 3759 (1978).

Traditional techniques and apparatus can be employed to form the liposomes according to the invention. These techniques are described in, for example, Chapter IV of the work entitled "Methods in Cell Biology", edited by David M. Prescott, Volume XIV, 1976, Academic Press, New York, page 33, et seq.

Another method of encapsulating the active Compounds I and II into a liposome involves casting a film of phospholipid (with or without a charged lipid) by evaporation from a solution in an organic solvent, and then dispersing the film in a suitable aqueous medium. In the case of lipid-soluble, biologically active compounds, that is, those which associate with the lipid layers rather than with the aqueous phase of the liposomes, the compound is usually cast as a film together with a phospholipid, using a common organic solvent. In the case of water-soluble, biologically active compounds, the compound is typically encapsulated in liposomes by dispersing a cast phospholipid film with an aqueous solution of the compound. The encapsulated compound is then separated from the free compound by centrifugation, chromatography or some other suitable procedure.

The lipophilic end of Compounds I and II enhance the incorporation of the compounds into liposomes. Compounds I and II are preferably incorporated into a liposome having a bilayer membrane consisting essentially of 1-palmitoyl-2-oleoyl-phosphatidyl choline (PC) and dioleoyl phosphatidyl glycerol (PG) in a weight ratio of about 5:1 to 1:1, preferably about 7:3. These compounds are commercially available from Avanti Polar Lipids, of Pelham, Ala.

Preferred methods which can be used to encapsulate Compounds I and II into a liposome are described in U.S. Pat. No. 4,370,349 which is incorporated herein by reference. The methods comprise either: (1) dissolving the necessary substances in a suitable solvent and then freeze-drying the solution, storing the resulting freeze-dried mixture, and, when desired, reconstituting it into an aqueous liposome preparation, or (2) preparing an aqueous liposome preparation by any known method and freeze-drying the preparation. When desired, the freeze-dried product can be made up into an aqueous liposome preparation. The freeze-dried mixtures disperse easily when shaken with an aqueous medium, and use of the freeze dried liposomes results in liposome preparations having a narrower size distribution than a corresponding preparation obtained by dispersing a cast film. This is advantageous to the reproducibility of the therapeutic effect of liposome preparations. Generally, the compositions in the form of liposomes can contain, in addition to Compounds I and II, any constituents, stabilizers, preservatives, excipients, or other active substances capable of being used in the injectable solutions or emulsions presented previously for administration of muramyl peptide compounds.

Delivery

Compounds I and II, preferably incorporated into liposomes, may be used for their adjuvant and/or antitumor activity, and may be administered orally or parenterally, preferably by injection.

The invention relates in particular to medicinal adjuvant and antitumor compositions, containing Compounds I and/or II, in association with a pharmaceutically acceptable carrier vehicle. Compositions of this type which are particularly preferred are constituted by the injectable solutions containing an effective immunomodulating amount of the product of the invention. Sterile solutions in an aqueous, preferably isotonic liquid, such as saline isotonic solutions or isotonic solutions of glucose, are advantageously used for this purpose. A simple solution in distilled water can also be used. It is also possible to use injection media containing an oily phase, especially water-in-oil emulsions. Such emulsions are obtained in particular with metabolizable vegetable oils, such as are described in the French Patent Application No. 75-04003. That French patent application corresponds to the U.S. co-pending patent application Ser. No. 656,738 of Audibert et al., filed on Feb. 9, 1976, based on said French priority patent application Ser. No. 75-04003. The preferred carrier vehicle is the freeze-dried liposomes described above.

The adjuvant and antitumor compositions of the invention may also be administered in various forms, by using for this purpose vehicles suitable for the selected method of administration. For example, unit dosage forms will be used in the form of cachets, compressed tablets or hard or soft gelatine-capsules, for oral administration, and aerosols or gels for the application to mucous membranes.

The compositions may also be in lyophilized form so as to permit the extemporaneous preparation of the adjuvant and antitumor compositions. A pharmaceutically advantageous form comprises unit doses of about 200 micrograms to 10 milligrams of Compound I or II per meter$^2$ of body surface area.

Manufacture

Compounds of the invention, for example, 4-O-[2-acetamido-2-deoxy-$\beta$-D-glucopyranosyl]-2-acetamido-2-deoxy-3-O-[D-2-propanoyl-L-alanyl-D-isoglutaminyl-L-alanyl-1,2-dipalmitoyl-sn-glycerol]-D-glucopyranose (GlcNAcMurNAc-L-Ala-D -isoGln-L-Ala-DPG (Compound IIA), may be prepared from commercially available materials, in about nine major steps. The steps do not necessarily have to be performed in the order described as will become apparent from the description below.

The first step involves the preparation of a blocked amino acid-diacyl glycerol. This is the lipophilic portion of Compound II attached to the C-terminus of the spacer group X, e.g., an amino acid residue. For example, in one embodiment this residue would be blocked-L-alanyl-1,2-dipalmitoyl-sn-glycerol.

The blocked amino acids or peptides employed as starting materials in the synthesis are either commercially available in the blocked form or are obtained by known methods of peptide chemistry. Blocking groups or protecting groups that can readily be split off are those known from peptide and sugar chemistry. For hydroxy groups the following are suitable examples: acyl radicals, for example lower alkanoyl radicals, such as acetyl; aroyl radicals, such as benzoyl; and especially radicals derived from carbonic acid derivatives, such as benzyloxycarbonyl or lower alkoxycarbonyl, or alkyl, especially tert-butyl, benzyl, optionally substituted by nitro, (lower) alkoxy or by halogen, triphenylmethyl or tetrahydropyranyl, each optionally substituted by halogen or by lower alkoxy such as methoxy, or optionally substituted alkylidene radicals that bond the oxygen atoms in the 4- and 6-position. Such alkylidene radicals are preferably a lower alkylidene radical, e.g., the methylidene, isopropylidene, or propylidene radicals, or alternatively, an optionally-substituted benzylidene radical.

For blocking C-terminal carboxy groups, suitable moieties include tert-butyl, benzyl, or benzhydryl. For protection of free amino groups, tert-butyloxycarbonyl or benzyloxycarbonyl groups can be used.

These blocking groups can be cleaved in a manner known in the art, such as acid hydrolysis. Benzyl or benzylidene radicals also can be removed by hydrogenolysis, for example using hydrogen in the presence of a noble metal catalyst, such as a palladium or platinum catalyst.

The second step in the preparation of a compound of the invention involves removal of the blocking group to form X-diacyl-glycerol, where X, for example, is an amino acid residue as described above, such as L-alanine. For example, a preferred component is L-alanine-1,2-dipalmitoyl-sn-glycerol (L-Ala-DPG).

The third step involves isolation of the disaccharide moiety GlcNAcMurNAc. Several methods are known in the art for obtaining this disaccharide moiety. One method involves the isolation from a suitable bacteria, for example *Micrococcus lysodeikticus* (dried cells are commercially available from Sigma Chemical Co., St. Louis, Mo.). The disaccharide that is obtained is N-acetylglucosaminyl-N-acetylmuramate. The isolation of this disaccharide from a biomass of *Micrococcus lysodeikticus* is known and described in the literature. It involves enzymatic hydrolysis of the cell walls obtained from the biomass of *Micrococcus lysodeikticus* by means of trypsin and lysozyme and a further purification in a column packed with Dowex® 1×8 (acetate form) 200–400 mesh (O. Hoshino, U. Zenavi, P. Sinay, R. W. Jeanloz, *J. Biol. Chem.* 247, No. 2, 381 (1972); and N. Sharon, T. Osawa, H. M. Flowers, R. W. Jeanloz, *J. Biol. Chemistry,* 241, 223 (1966). Also, see, U.S. Pat. No. 4,427,659, which is incorporated herein by reference. A second method by which the disaccharide moiety GlcNAcMurNAc and disaccharide peptides may be obtained is by means of total chemical synthesis. See for example S. Kusomoto et al., *Bull. Chem. Soc. Jpn.,* 59, 1414 (1986); M. Kiso et al., *Carbohydrate Res.,* 104, 253 (1982); and A. Hasegawa et al., *Carbohydrate Res.,* 100, 234 (1982); S. Kusumoto et al., *Tetrahedron Letters,* 45, 4407 (1978); and R. Fhyuri et al., *Agric. Biol. Chem.,* 50 2561 (1986). A third method by which the disaccharide moiety, preferably linked to appropriate amino acid residues, may be produced is through the use of recombinant DNA technology.

Enzymatic methods have also been described, by which disaccharide peptides may be obtained. Such methods generally yield compounds containing the natural L-meso-2,5-diaminopimelic acid at the third amino acid position herein designated by "X". See, for example, S. Kawata et al., *Agric. Biol. Chem.,* 48, 1783 (1984); D. Keglevic et al., *Biochimica et Biophysica Acta,* 585, 273 (1979). Through the use of an enzymatic hydrolysis using gamma-D-glutamyl-meso-diaminopimelate endopeptidase I isolated from *Bacillus sphaericus* 9602 or other appropriate bacterium, it is also possible to enzymatically isolate the disaccharide dipeptide GlcNAc-MurNAc-L-Ala-D-isoGln. [See M. Guinand et al., *Eur. J. Biochem.,* 143, 359 (1984)]. Reference is also made to U.S. Pat. Nos. 4,395,399; 4,515,891; and 4,545,932; incorporated herein by reference.

In the disaccharide isolated above, $R^1$ and $R^2$ are both —CH$_3$, forming acetyl groups on both the muramyl and glucosamyl functionalities. The analogous compounds, where $R^1$ is a ($C_1$–$C_9$)alkyl group and $R^2$ is a ($C_1$–$C_5$)alkyl group, can be prepared by methods known in the art. For example, the acetyl group can be hydrolyzed by a strong base, for example, as described in P. H. Gross and R. W. Jeanloz, *J. Org. Chem.*, 32, 2761 (1967). Then an acylating agent, corresponding to the $R^1$ or $R^2$ which is desired to be introduced, such as an acid anhydride or chloride, may be used to attach the desired $R^1$ or $R^2$ group to the muramyl or glucosaminyl functionality.

The next step involves the preparation of the dipeptide-Y-D-isoglutamine, which is blocked on both ends. For example, in Compound IIA where Y is L-alanine, BOC-L-alanyl-D-isoglutamine, commercially available from United States Biochemical Co. of Cleveland, Ohio (USBC), must be treated in a manner known in the art to terminate the C-terminus isoglutamine residue with a suitable blocking agent, such as a benzyl ester (—OBn). BOC refers to N-tert-butoxycarbonyl, a blocking group. Thus, BOC-L-Ala-D-isoGln-OBn is preferably formed.

The next step involves the removal of the blocking group from the alanine by a known method to form, for example, L-Ala-D-isoGln-OBn. The next step involves coupling the N-acylglucosamine-N-acylmuramyl functionality with the alanine-isoglutamine moiety. The condensation reaction is conducted in an inert solvent medium, in the presence of a condensation agent, preferably Woodward's Reagent K (N-ethyl-5-phenyl-isoxazolium-3'-sulphonate), at a temperature of about 0° C. to 25° C. in one stage. See, U.S. Pat. No. 4,395,399.

The next step involves removal of the blocking group by conventional means to form the unblocked disaccharide-dipeptide, for example, 4-O-[2-acetamido-2-deoxy-β-D-glucopyranosyl]-2-acetamido-2-deoxy-3-O-[D-2-propanoyl-L-alanyl-D-isoglutamine]-D-glucopyranose (GlcNAcMurNAc-L-Ala-D-isoGln).

The final step involves the coupling of the unblocked disaccharide-dipeptide, GlcNAcMurNAc-L-Ala-DisoGln, with the amino acid-diacyl glycerol component by conventional techniques to form the Compound IIA.

A similar compound to Compound IIA, 4-O-[2-acetamido-2-deoxy-β-D-glucopyranosyl]-2-acetamido-2-deoxy-3-O-[D-2-propanoyl-L-alanyl-D-isoglutaminyl-D-alanyl-1,2-dipalmitoyl-sn-glycerol]-D-glucopyranose (GlcNAcMurNAc-L-Ala-D-isoGln-D-Ala-DPG) (Compound IIB) is prepared by the same procedure described for Compound IIA, except that the final synthetic step involves the coupling of the disaccharide dipeptide, GlcNAcMurNAc-L-Ala-D-isoGln, to D-Ala-DPG rather than to L-Ala-DPG.

A compound according to Formula I, where the lipophilic group is attached via an amide linkage (designated NHDPG), for example, 4-O-[2-acetamido-2-deoxy-β-D-glucopyranosyl]-2-acetamido-2-deoxy-3-O-[D-2-propanoyl-L-alanyl-D-isoglutaminyl-L-alanyl-2-(1,3-dipalmitoyloxy) propylamide]-D-glucopyranose, (GlcNAcMurNAc-L-Ala-D-isoGln-L-Ala-NHDPG) (Compound IA), is prepared by the same general approach used for the synthesis of compounds IIA and IIB, i.e., by the coupling of the disaccharide dipeptide, GlcNAcMurNAc-L-Ala-D-isoGln, to the lipophilic alanine amide, L-Ala-NHDPG. The disaccharide dipeptide is prepared as described in the synthesis of Compound IIA, while the required amide is prepared by the following three-step synthetic sequence:

(A) The blocked amino acid, BOC-L-Ala, is coupled with serinol (SerOH) by conventional means to give BOC-L-Ala-SerOH.
(B) BOC-LD-Ala-SerOH is reacted with two moles of palmitic acid to yield the dipalmitate, BOC-D-Ala-NHDPG.
(C) The BOC-protecting group is removed by conventional means to form the unblocked lipophilic alanine amide, L-Ala-NHDPG.

The final synthetic step involves the coupling of the GlcNAcMurNAc-L-Ala-D-isoGln with the lipophilic amide by conventional techniques to form the Compound IIA.

Compound I or II is preferably encapsulated into liposomes as described herein above. Preferably the compound of the invention is combined with phosphatidyl choline and phosphatidyl glycerol. Typically the phospholipids are dissolved in tert-butanol at a concentration of about 100 mg per ml. Appropriate amounts of the PC and PG in tert-butanol are mixed to give a weight ratio of about 7:3. Compound I and/or II is weighed out and added to a given volume of the lipids to give a final concentration of, for example, about 1 mg per 5 ml. The material is then passed through a millipore filter and the composition is dispensed into vials. The vials are frozen, typically at −20° C. and lyophilized typically at about 20° C. for 18 hours. The vials are then sealed under an inert gas, such as argon.

The present invention is further described by way of the following non-limiting examples:

PREPARATION OF GlcNAcMurNAc-L-Ala-D-isoGln-D-Ala-DPG

EXAMPLE 1

BOC-L-Ala-DPG

In a 25 ml-round bottomed flask (RBF) was placed 208.64 mg (1.103 mMol) of BOC-L-alanine, 570.0 mg (1.002 mMol) of 1,2-dipalmitoyl-sn-glycerol (DPG, Sigma), 63.14 mg (0.517 mMol) of 4-dimethylaminopyridine (DMAP) (Aldrich Chemical Co., Milwaukee, Wis.), and 230.04 mg (1.200 mMol) of 1-ethyl-3-(3-dimethylaminopropyl)carbodiimide hydrochloride (EDCI). BOC is the abbreviation for N-tert-butoxycarbonyl, a blocking group. Methylene chloride ($CH_2Cl_2$) was added bringing the final volume to 14 ml. The mixture was stirred in an ice-water bath for one hour, then at room temperature (RT) overnight.

After stirring overnight, the solvent was removed on a rotary evaporator under aspirator vacuum to yield a white solid, which was partitioned between 20 ml of ethyl acetate (EtOAc) and 10 ml of water. The water layer was extracted with another 20 ml of EtOAc. The organic fractions were combined and extracted with 2–20 ml of saturated aqueous sodium bicarbonate ($NaHCO_3$) followed by 2×20 ml of water and then dried over sodium sulfate ($Na_2SO_4$). The solvent was removed on a rotary evaporator to yield 648 mg (87%) of BOC-L-Ala-DPG as a white solid.

EXAMPLE 2

L-Ala-DPG 630 mg (0.85 mMol) of BOC-L-Ala-DPG was dissolved in 15 ml of $CH_2Cl_2$ to which was added 5.0 ml of trifluoroacetic acid (TFA). The solution was stirred at RT for two hours, then concentrated to dryness on a rotary evaporator to yield a tan oil that was dissolved in 10 ml of hexane and concentrated to dryness on a rotary evaporator. The process was repeated several times to remove the last traces of TFA. This material was then dried under high vacuum to yield 606.7 mg of L-Ala-DPG trifluoroacetate as an off-white solid.

EXAMPLE 3
GlcNAcMurNAc

Dried cells (15.0 grams) of *Micrococcus lysodeikticus* (commercially available from Sigma Chemical Co., St. Louis, Mo.), was suspended in 200 ml of distilled water and disrupted by stirring at high speed with 250 g of 0.1 mm glass beads for 90 minutes at 4° C. The cell wall skeletons (CWS) were removed from the glass beads by decantation and then centrifuged at 1200×g for 30 minutes. The supernatant was removed from the pellet (intact cells), then centrifuged at 10,000×g for 50 minutes. The supernatant was removed and the resulting pellet (crude CWS) was washed three times by suspension in 100 ml of distilled $H_2O$ and centrifugation at 10,000×g for 70 minutes. The resulting pellet was suspended in 150 ml of distilled water and then placed in a boiling water bath for 30 minutes.

After cooling to ambient temperature, the resulting slurry was centrifuged at 10,000×g. The supernatant was removed and the pellet slurried in 60 ml of 0.05M ammonium acetate ($NH_4OAc$) buffer (pH 7.60). The resulting slurry was treated with 10.0 mg of porcine pancreas trypsin (Sigma, 14,600 BAC units/mg), and incubated at 37° C. for 20 hours. After several washes with distilled $H_2O$, the CWS pellet was slurried in 60 ml of 0.05M $NH_4OAc$ buffer (pH 6.30), treated with eggwhite lysozyme (Sigma, 56,000 units/mg, 10.0 mg), and incubated at 37° C. for 19 hours.

The crude preparation was dialyzed to remove the enzymes and undigested cell walls. Final purification was achieved by ion exchange chromatography on Dowex®-1 resin (acetate form) by elution with an acetic acid (HOAc) gradient. The column fractions were pooled based on UV absorbance and thin layer chromatography (TLC) (Merck silica, $CHCl_3/MeOH/H_2O/NH_4OH$, 50:39:8:3, 5% $H_2SO_4/EtOH$ and heating). Positive identification of the disaccharide product was obtained from colorimetric analysis of muramic acid and total hexosamines, and fast atom bombardment (FAB) mass spectrometry. Approximate yields were 120 mg GlcNAcMurNAc from 15 g of dried cells.

EXAMPLE 4
BOC-L-Ala-D-isoGln-OBn

Benzyl alcohol (77.0 mg, 0.71 mMol), DMAP (33.0 mg, 0.27 mMol), and BOC-L-alanyl-D-isoglutamine (USBC, 159.0 mg, 0.50 mMol) were dissolved in 5 ml of $CH_2Cl_2$ and 2 ml of N,N-dimethylformamide (DMF). This solution was cooled in an ice-water bath to 4° C., treated with EDCI (118.0 mg, 0.61 mMol) and stirred at 4° C. for 30 minutes, then at room temperature for 15 hours. After removing the solvents in the rotary evaporator, the residue was partitioned between 20 ml of EtOAc and 10 ml of $H_2O$. The layers were separated and the aqueous layer extracted with another 20 ml of EtOAc. The organic fractions were combined, then successively extracted with saturated $NaHCO_3$ (2×20 ml) and $H_2O$ (2×20 ml). After drying over $Na_2SO_4$, the solvent was removed on the rotary evaporator leaving a waxy solid, which was recrystallized from EtOAc-petroleum ether to yield 141 mg (69%) of BOC-L-Ala-D-isoGln-OBn as white fluffy solid.

EXAMPLE 5
L-Ala-D-isoGln-OBn

BOC-L-Ala-D-isoGln-OBn (120 mg, 0,294 mMol) was treated with 10 ml of 1N HCl/HOAc and the resulting solution stirred at RT for 2 hours. The solvent was then removed on the rotary evaporator to yield a colorless oil, which was taken up in 3 ml of MeOH, then precipitated by the dropwise addition of 20 ml of diethyl ether. After stirring for one hour at RT, the product was collected on a filter, washed with ether, then dried under high vacuum to yield 88 mg of the hydrochloride salt of L-Ala-D-isoGln-OBn as a white solid.

EXAMPLE 6
Coupling of GlcNAcMurNAc with L-Ala-D-isoGln-OBn

A total of 200 mg of GlcNAcMurNAc (MW 496.47, 0.405 mMol) was dissolved in 15 ml of DMF and then treated with 0.95 ml of a solution containing 42.94 mg/ml of triethylamine (TEA) in DMF (0.403 mMol). The solution was cooled with magnetic stirring in an ice bath and then treated with 139.63 mg (95% pure, 0.524 mMol) Woodward's Reagent K. The slurry was then stirred in an ice-water bath for one hour, then at room temperature for 10 minutes. Then a solution containing 152.3 mg (0.443 mMol) of the HCl salt of the L-Ala-D-isoGln-OBn in 8.0 ml of DMF to which was added 1.05 ml (0.443 mMol) of the TEA/DMF solution was added via a pressure equalizing funnel over a period of 10 minutes. The solution was stirred at RT for 18 hours and then allowed to stand for an additional 96 hours. The reaction was followed during this time by TLC (Merck silica, $CHCl_3/MeOH/H_2O/Con\ NH_4OH$, 50:25:4:2, 5% $H_2SO_4/EtOH$ and heat) and allowed to go as far as possible to completion.

The DMF was removed in a rotary evaporator under high vacuum (approximately 50 microns) at 25° C. to yield a reddish oil that was further dried under high vacuum.

The oil was taken up in 5 ml of $H_2O$ and applied to a 1.7×7 cm column of Dowex®1×8 resin (200–400 mesh, acetate form). The column was washed with 50 ml of $H_2O$ and the entire colorless eluate applied to a 1.7×7 cm column of Amberlite®IR-120 P resin (16–20 mesh, H+ form). The column was washed with 50 ml of $H_2O$ and the eluate and washings were combined. This material was taken to dryness in a rotary evaporator under aspirator vacuum at 25° C. to yield a colorless oil. This was dried under high vacuum (50–75 microns) overnight during which time it solidified to a glassy solid. This was taken up in 20 ml of $H_2O$ and lyophilized to yield 181 mg of GlcNAcMurNAc-L-Ala-D-isoGln-OBn as a snow white fluffy solid.

EXAMPLE 7
GlcNAcMurNAc-L-Ala-D-isoGln

The protected material prepared (170 mg) in Example 6 was dissolved in a solution of $H_2O$ (30 ml) and acetic acid (1.0 ml). The solution was added to 100 mg of 5% Pd/C (by weight of the palladium, C is powdered charcoal, from Matheson, Coleman, and Bell of Norwood, Ohio) in a 500 ml Parr hydrogenation bottle and hydrogenated at 20 PSIG for 24 hours. The catalyst was removed and washed with water (3×10 ml), and the filtrate and washings were combined and lyophilized to yield 150 mg (100%) of GlcNAcMurNAc-L-Ala-D-isoGln as a white solid. The product was further dried under high vacuum for 48 hours then tightly capped and stored at 4° C.

EXAMPLE 8
Coupling of GlcNAcMurNAc-L-Ala-D-isoGln to L-Ala-DPG to yield GlcNAcMurNAc-L-Ala-D-IsoGln-L-Ala-DpG (IIA)

1-Hydroxybenzotriazole (HOBT) (31.35 mg, 0.232 mMol) and EDCI (44.26 mg, 0.231 mMol) were placed in a 50 ml-RBF. To this was added a solution containing the disaccharide dipeptide as prepared in Example 7 (139.13 mg, 0.20 mMol) in 7 ml DMF and 5 ml $CH_2Cl_2$. The resulting solution was stirred at RT for 30 minutes.

A triethylamine (TEA) solution was prepared by dissolving 202 mg (0.28 ml) of TEA in DMF and adjusting the final volume to 10 ml.

L-Ala-DPG (150.8 mg, 0.20 mMol) was dissolved in 1 ml of $CH_2Cl_2$. DMF (1 ml) was added, followed by 1 ml of the TEA solution. The resulting solution was added to the activated disaccharide dipeptide solution, the vessel was securely capped and stirred for 72 hours.

The reaction was followed by TLC (see Example 6) and stopped at 72 hours. The reaction mixture was then split into two portions, one of 5 ml, the other of 10 ml. These samples were concentrated to dryness on a rotary evaporator at room temperature under high vacuum. They were then further dried in a desiccator for 24 hours during which time both samples dried to yellow-orange solids.

For purification, the smaller portion was partitioned between 25 ml $H_2O$ and 25 ml EtOAc. The layers were separated, and the organic layer was extracted with 2×10 ml of $H_2O$ and the washes added to the aqueous layer. The aqueous fraction was then washed with 25 ml of EtOAc, the layers were separated, and the aqueous layer was concentrated to half volume on a rotary evaporator, then extensively dialyzed against $H_2O$ through an Amicon YM-5 membrane at 30–35 psi.

TLC analysis (see Example 6) of the inner dialysate showed a single spot. This material was then filtered through Whatman® #2 paper then lyophilized to yield 35 mg of product as a cream colored solid.

LARGE SCALE PREPARATION OF GlcNAcMurNAc-L-Ala-D-isoGln-L-Ala-DPG (IIA)

EXAMPLE 9

BOC-L-Ala-DPG (III)

1,2-Dipalmitoyl-sn-glycerol (Sigma, 2.845 g, 5.0 mMol), BOC-L-alanine (USBC, 966 mg, 5.1 mMol), and DMAP (Aldrich, 357 mg, 2.93 mMol) were dissolved in 50 ml of $CH_2Cl_2$. EDCI (Sigma, 1.174 g, 6.12 mMol) was added, and the solution was stirred at RT for 17 hours. After removal of the solvent on a rotary evaporator, the residue was partitioned between 150 ml of EtOAc and 75 ml of $H_2O$, the layers separated and the organic layer extracted with saturated aqueous $NaHCO_3$ (3×50 ml), then with $H_2O$ (3×75 ml). After drying over $Na_2SO_4$, the solvent was removed on the rotary evaporator and the residue further dried under high vacuum to yield 3.59 g (97%) of product as a slightly off-white solid.

TLC (silica; $CHCl_3$/MeOH/$H_2O$, 130:45:7; HCl spray, then ninhydrin) of the product revealed a single spot of $R_f$ 0.95.

L-Ala-DPG (IV)

The protected alanine ester (III) (2.50 g, 3.38 mMol) was dissolved in 75 ml of $CH_2Cl_2$, then treated with 25 ml of TFA. After standing at room temperature for two hours, the solvents were removed on the rotary evaporator to leave a tan oil that was repeatedly taken up in 20 ml-portions of hexane then concentrated to dryness on the rotary evaporator. After extensive drying under high vacuum, 2.44 g (95.7%) of Compound IV was obtained as its trifluoroacetate salt.

BOC-L-Ala-D-isoGln-OBn (V)

BOC-L-Ala-D-isoGln (USBC, 1.587 g, 5.0 mMol), benzyl alcohol (540.7 mg, 5.0 mMol), and DMAP (305 mg, 2.5 mMol) were dissolved in 40 ml of $CH_2Cl_2$ and 10 ml of DMF, and the resulting solution was cooled in an ice-water bath to 4° C. with magnetic stirring. EDCI (1.150 g, 6.00 mMol) was added, and the reaction stirred in the ice bath for one hour, then at room temperature for 17 hours. After removal of the solvents on the rotary evaporator, the oily residue was partitioned between 50 ml of $H_2O$ and 150 ml of EtOAc, the layers separated, and the organic layer further extracted with saturated aqueous $NaHCO_3$ (3×50 ml) and $H_2O$ (3×50 ml). After drying over $Na_2SO_4$, the solvent was removed on the rotary evaporator to yield a colorless oil that was further dried under high vacuum, during which it solidified to a waxy solid. Recrystallization from EtOAc-hexane yielded 1.318 g (65%) of Compound V as a snow-white solid.

A TLC (silica; EtOAc/pyridine/HOAc/$H_2O$, 30:2:0.6:1; HCl spray, then ninhydrin) of the product revealed a single spot of $R_f$ 0.90.

L-Ala-D-isoGln-OBn (VI)

The protected dipeptide ester V (2.08 g, 5.10 mMol) was treated with 100 ml of 1N HCl/HOAc, and the resulting solution was allowed to stand at room temperature for two hours. After removal of the solvents on the rotary evaporator and further drying under high vacuum, the product was crystallized from MeOH-ether to yield 1.68 g (95.8%) of Compound VI as its hydrochloride salt.

Preferred Method of Preparation of GlcNAcMurNAc (VII)

Cell Disruption

*Micrococcus lysodeikticus* (Sigma, 200 g), in the form of dried cells, was suspended in distilled water for 24 hours, then disrupted with a Microfluidics Corporation laboratory Microfluidizer® (Model M-110Y). This was driven by a Powerex® GI-25 air compressor at a normal operating air pressure of 82 PSIG, which resulted in a hydraulic pressure of 19,000 PSIG. Approximately ten passes through the interaction chamber at these operating conditions were required to effect nearly total (95–98%) disruption of the cells. The resulting slurry was then centrifuged for 30 minutes at 1000×g, the supernatant (containing CWS) removed from the small pellet (intact cells), then centrifuged for two hours at 10,000×g. The resulting supernatant was carefully removed by decantation and discarded. The white, somewhat greasy, pellet was suspended in 1,500 ml of distilled water, then carefully warmed with magnetic stirring to 90° C. and held at that temperature for 30 minutes. After cooling to RT, the slurry was centrifuged at 10,000×g for 2.5 hours, and the supernatant carefully removed and discarded. The resulting pellet (containing CWS) was then washed once by suspension in a total of 2000 ml of water, followed by centrifugation at 10,000×g for 2.5 hours.

Trypsin Treatment

The pellet from above was suspended in 2000 ml of 0.05M sodium phosphate buffer (pH 7.60) and the pH of the slurry corrected by 7.60 by the addition of 10N NaOH. Trypsin (porcine pancreas, type IX, 300 mg, 17,000 BAEE units/mg protein) and toluene (10 drops) were added and the resulting slurry incubated at 37° C. for 20 hours. The pH was then corrected to 7.60 with 10N NaOH, an additional 100 mg of trypsin was added, and the mixture again incubated at 37° C. for 24 hours. The slurry was then centrifuged at 10,000×g for 2.5 hours, the supernatant carefully removed and discarded, and the white pellet (containing deproteinized CWS) washed several times with water by suspension-centrifugation until a ninhydrin test of the supernatant was negative.

Lysozyme Digestion

The pellet (i.e., deproteinized CWS) from above was suspended in 1500 ml of 0.1M $NH_4OAc$ (pH 6.30), and the pH of the slurry was corrected to 6.30 with dilute HOAc. Lysozyme (egg-white, 400 mg, 49,000 U/mg) and toluene (5 drops) were added, and the slurry was incubated at 37° C. for 24 hours, during which time the slurry cleared up considerably. Then, an additional 200 mg of lysozyme was added, and the mixture was incubated for another 24 hours at 37° C. The reaction mixture was then centrifuged at 10,000×g for 2.5 hours. The clear, yellowish supernatant was removed from the small pellet, then dialyzed through an Amicon PM-10 membrane. The colorless outer dialysate was concentrated to dryness on the rotary evaporator, and the resulting residue repeatedly dissolved in water, then concentrated to dryness in order to remove the last traces of the $NH_4OAc$ buffer. The yellow syrupy residue was finally dissolved in 400 ml of water, then lyophilized to yield 20.8 g of a yellow, gummy solid.

Purification of Disaccharide

The entire 20.8 g of the lysozyme digest from above was dissolved in 100 ml of water, then applied to a 4.3×63 cm column of Dowex® 1 (acetate form, 200-400 mesh) resin. The column was then eluted with a gradient comprised of 4000 ml of $H_2O$ (starting) and 4000 ml of 0.8N HOAc (final) at a flow rate of 3.5 ml/minute. Fractions of 21 ml were collected and analyzed by TLC as described in Example 3A. The desired fractions were then pooled, concentrated to dryness on the rotary evaporator, then redissolved in water and lyophilized to yield 2.60 g of crude product as a slightly off-white solid.

For final purification, the 2.60 g of crude disaccharide was dissolved in 25 ml of water, then applied to a 3×55 cm column of Dowex® 1 (acetate form, 200-400 mesh) resin. The column was then eluted with a gradient comprised of 2000 ml of $H_2O$ (starting) and 2000 ml of 0.8N HOAc (final) at a flow rate of 3.0 ml/minute. Fractions of ca. 21 ml were collected and were analyzed by TLC as above. The desired fractions were pooled, concentrated to dryness on the rotary evaporator, then redissolved in 50 ml of water and lyophilized to yield 2.243 g of pure product as a snow-white solid.

GlcNAcMurNAc-L-Ala-D-isoGln-OBn (VIII)

Prior to use, the DMF was dried over 4A molecular sieves, then distilled from ninhydrin. The TEA was distilled from sodium hydroxide (NaOH) pellets. Woodward's Reagent K was purified by dissolving 3.0 g of the commercial material (Aldrich) in 15 ml of 1N HCl, filtering through Whatman #2 paper, then precipitating by the addition of 120 ml of acetone. After filtering and washing with 100 ml of acetone, the reagent was dried under high vacuum for several hours.

The disaccharide Compound VII (2.00 g, 4.028 mMol) was dissolved in 100 ml of DMF, treated with TEA (0.62 ml, 447.5 mg, 4.431 mMol), cooled in an ice-water bath to near 4° C., then treated with Woodward's Reagent K (95%, 1.397 g, 5.24 mMol). The resulting slurry was stirred in the ice-water bath for one hour, then at room temperature for 10 minutes. Then, a solution containing the dipeptide benzyl ester (VI) (1.523 g, 4.43 mMol) and TEA (447.42 mg, 0.616 ml) in 50 ml of DMF was added via a pressure equalizing addition funnel over a period of 30 minutes. After the addition was completed, the reaction mixture was stirred at room temperature for a total of 120 hours, during which the progress of reaction was monitored by TLC (see Example 6). The solvent was then removed on the rotary evaporator and the oily residue further dried under high vacuum. This was then taken up in 50 ml of $H_2O$, then applied to a 2.5×17 cm column of Dowex 1×8 resin (200-400 mesh, acetate form) and eluted with 500 ml of $H_2O$. The entire eluate was concentrated to ca. 50 ml, then applied to a 2.5×17 cm column of Dowex 50×8 resin (100 mesh, $H^+$form) and eluted with 500 ml of $H_2O$. The eluate was concentrated to ca. 50 ml, then lyophilized to yield 2.25 g (71%) of Compound VIII as a snow-white solid.

GlcNAcMurNAc-L-Ala-D-isoGln (IX)

The disaccharide dipeptide benzyl ester (VIII) (2.20 g, 2.80 mMol) was dissolved in 150 ml of $H_2O$ and 3.0 ml of glacial acetic acid. To this was added 300 mg of 5% Pd/C, and the resulting slurry was hydrogenated at room temperature and 40 PSIG for 40 hours. The catalyst was then removed by filtration through a Celite pad, washed with $H_2O$ (3×10 ml), and the filtrate and washings combined, concentrated to ca. 50 ml, then passed through a 1 ml column of Detoxi-Gel®(Pierce) at a flow rate of 8 ml/hr. The column was washed with 10 ml of $H_2O$, and the eluate and washings were combined, then lyophilized to yield 1.86 g (95.5%) of Compound IX as a white powder.

GlcNAcMurNAc-L-Ala-D-isoGln, L-Ala-DPG (IIA)

The DMF and TEA used in this preparation were purified as described in the preparation of VIII. The disaccharide dipeptide IX (1.531 g, 2.20 mMol) was dissolved in 70 ml of DMF, then diluted with 50 ml of $CH_2Cl_2$. To this was then added HOBT (Aldrich, 387.4 mg, 2.53 mMol) and EDCI (485 mg, 2.53 mMol), and the resulting solution was stirred at room temperature for one hour. Then, a solution containing 1.659 g (2.2 mMol) of the ester (IV) and 225 mg (0.31 ml, 2.20 mMol) of TEA in 20 ml of $CH_2Cl_2$ was added dropwise over a period of 5 min. The resulting solution was stirred at room temperature for 24 hours, then treated with an additional 100 mg of EDCI and stirred for another 48 hours. The solvents were removed on the rotary evaporator and the oily residue further dried under high vacuum for several hours, during which it solidified to a yellow waxy material. This was then washed three times by suspension in 150 ml-portions of EtOAc and centrifugation at 200×g. After drying under high vacuum, the pellet was suspended in 1000 ml of distilled $H_2O$, then extensively dialyzed against distilled $H_2O$ in an Amicon ultrafiltration cell through an Amicon YM-10 membrane. The inner dialysate was then diluted to 2000 ml with distilled $H_2O$, filtered through a triple layer of paper (Labconco Corp. #fA-754448), concentrated to ca. 600 ml on the rotary evaporator, and lyophilized to yield 1.60 g of Compound IIA as a white, electrostatic powder.

For final purification, 52.8 mg of the above product was dissolved in 1.0 ml of $CHCl_3/MeOH/H_2O$, 2:3:1, then applied to a 0.7×29 cm column of Sephadex LH-20-100 resin that had been swollen and packed in the same solvent. The column was eluted at a flow rate of 0.33 ml/min, and fractions of the eluate were collected and assayed by TLC (see Example 6). The appropriate fractions were combined, then applied directly to a 1×8 cm column of BioRad Cellex D resin (acetate form).

This column was then washed with 30 ml of solvent, and the combined eluate and washings concentrated to near dryness on the rotary evaporator, treated with 75 ml of H$_2$O, and lyophilized to yield 35 mg of GlcNAc-MurNAc-L-Ala-D-isoGln-L-Ala-DPG (GMTP-DPG) as a white powder.

| Analysis for product as the dihydrate: | | | | | |
|---|---|---|---|---|---|
| C$_{65}$H$_{116}$N$_6$O$_{21}$·2H$_2$O | | | | | |
| Calculated: | C | 57.67 | H | 8.93 | N | 6.21 |
| Found: | C | 57.89 | H | 8.58 | N | 5.91 |

FAB-MS, m/c 1340 (M + 23), 1318 (M + 1), 1300 (M − 18 + 1)

EXAMPLE 10
Preparation of Liposomes

The compound (IIA) was encapsulated into liposomes using the following procedure. One mg of IIA as prepared in Example 9 was combined with 175 mg of 1-palmitoyl-2-oleoyl phosphatidyl choline (PC) and 75 mg of 1,2-dioleoyl phosphatidyl glycerol (PG), both commercially available from Avanti Polar Lipids, Pelham, Ala. The PC and PG were previously dissolved in tert-butanol at a concentration of 100 mg lipid per ml, thus giving a 7:3 weight ratio of PC:PG in tert-butanol. Tert-butanol was then added to the 1 mg IIA; 175 mg PC; 75 mg PG to give a final volume of 5.0 ml. The IIA and lipid mixture was passed through a sterile millipore 0.22μ filter to remove any contaminants present. The filtrate was collected in a clean, sterile, round bottom flask which was capped with aluminum foil after filling. Five ml of the filtered mixture containing 1 mg of IIA was dispensed into 10 ml vials. After the vials were filled, they were covered with sterile rubber serum stoppers. Each of the stoppers includes a slit in one side so that air can enter and leave the vial during lyophilization and stoppering. Sterile aluminum foil was placed over the vials and the vials were transferred to the tray drying chamber of the lyophilizer. The vials were then cooled to −20° C. until the tert-butanol lipid mixture was frozen (approximately 30 to 60 minutes). The refrigeration was then turned off and the tray heater set for 10° C. The vials were then lyophilized for 18 hours. The lyophilizer containing the vials was purged with filtered sterile argon and evacuated three times. The lyophilizer containing the vials was then purged again with argon and the vials stoppered under argon at atmospheric pressure.

EXAMPLE 11
Adjuvant Activity of the Agent in Saline on Antibody Producing Cells in Combination with Particulate Antique The efficacy of the compound of the invention in inducing antibody response was evaluated in an immuno-compromised model using aged Balb/c mice and in normal mice using a suboptimal dose of the immunogen.

Aged, Balb/c mice (18 months old), representing an immunodeficient animal, were immunized intraperitoneally with an optimal inoculum of 1×10$^9$ sheep red blood cells (SRBC) either alone or mixed with 0.1 mg of MDP or 0.1 mg of Compound IIA. The spleen was removed on day 4 and assayed for plaque forming units.

The results (Table 1) indicated a total of 66×10$^3$ plaque forming units (PFU) per spleen for controls, 198×10$^3$ PFU per spleen for mice receiving SRBC mixed with 0.1 mg MDP and 442×10$^3$ PFU for mice receiving SRBC mixed with 0.1 mg. of a compound of the invention IIA. Similarly, young Balb/c mice were immunized intraperitoneally with a suboptimal dose of SRBC (1×10$^7$ cells) in saline or mixed with 0.01 of 0.1 mg of MDP or IIA.

The results (Table 1) indicate that on a weight basis IIA was 3 to 10 times more effective than MDP.

TABLE 1
COMPARISON OF THE ADJUVANT ACTIVITY OF MDP AND IIA

| AGE OF MICE | SRBC INOCULUM | MDP (mg/mouse) | IIA (mg/mouse) | PFU ×10$^3$ |
|---|---|---|---|---|
| 18 months | 1 × 10$^9$ | — | — | 66 |
| 18 months | 1 × 10$^8$ | 0.1 | — | 198 |
| 18 months | 1 × 10$^8$ | — | 0.1 | 442 |
| 3 months | 1 × 10$^7$ | — | — | 75 |
| 3 months | 1 × 10$^7$ | 0.01 | — | 100 |
| 3 months | 1 × 10$^7$ | 0.1 | — | 144 |
| 3 months | 1 × 10$^7$ | — | 0.01 | 184 |
| 3 months | 1 × 10$^7$ | — | 0.1 | 468 |

EXAMPLE 12
Antitumor Activity of IIA in Saline in the Meth A Sarcoma

BALB/C female mice, age 7 weeks, were injected subcutaneously with 1×10$^6$ Meth A tumor cells. Eight days later the animals were treated intravenously with either saline (control) or Compound IIA at a dose of 1, 10, or 100 micrograms (μg). Each group consisted of 4 animals. Tumor measurements were taken every 2 days for 10 days and the mice followed for 60 days until cured or death due to tumor occurred.

The results indicated a 10 to 15% decrease in tumor size on day 6 after therapy with a single dose of 1 to 10 μg of Compound IIA. A larger dose of 100 μg resulted in a 50% decrease in tumor growth at day 6 after therapy with one of four animals exhibiting complete regression of tumor.

EXAMPLE 13
Activation of Human Peripheral Blood Monocytes to the Tumoricidal State by IIA and Liposome Encapsulated IIA Monocyte tumoricidal activity was determined by the method of Fogler and Fidler (W. E. Fogler and I. J. Fidler, J. Immunol., 136; 2311–2317, 1986). Briefly, human peripheral blood monocytes were isolated by gradient centrifugation on 46% Percoll. Monocytes were then cultured in suspension for 18 hours in RPMI 1640 media containing 5% human sera with or without 1.0 μg/ml of Compound IIA at 1×10$^6$ monocytes/ml. After incubation monocytes were washed, and 1×10$^5$ or 5×10$^4$ monocytes allowed to attach to wells of a 96-well microplate for 1 hour, then the plate was washed to remove non-adherent cells; to this, 1×10$^4$ I$^{125}$ labeled A-375 tumor cells were added. Monocytes were cultured with tumor cells for 72 hours. At the end of the 72 hour co-culture period, the plates were washed to remove non-adherent-non-viable tumor cells and the remaining adherent viable I$^{125}$ labeled tumor cells determined by lysing the cells with sodium dodecyl sulfate and counting radioactivity in a Gamma Counter.

Activation of human peripheral blood monocytes by liposomes consisting of PC and PG (7:3) containing Compound IIA was determined as described above.

The effector:target cell ratio was 10:1. The cultures contained a final concentration of 1.0 μg/ml of MDP, Compound IIA or Compound IIA in liposomes. The results of these tests (Table 2) indicate that Compound IIA is more effective than MDP when used as a saline suspension or when encapsulated in liposomes.

TABLE 2

| | PERCENT CYTOTOXICITY[1] | | |
|---|---|---|---|
| EXPERIMENT | MDP[3] | COMPOUND IIA[4] | COMPOUND IIA[2] IN LIPOSOMES[5] |
| 1 | 38% | 59% | 73% |
| 2 | 27% | 37% | 44% |

[1]Percent cytotoxicity $\frac{A - B}{A} \times 100$
where A = CPM in wells with control monocytes;
B = CPM in wells with treated monocytes.
[2]Compound IIA in liposomes at a concentration of 1 mg/ml had no detectable endotoxin as determined by LAL assay with a sensitivity of 0.06 endotoxin units per ml.
[3]MDP purchased from Cal-Biochem.
[4]Compound IIA at a concentration of 1 mg/ml had no detectable endotoxin as determined by LAL assay with a sensitivity of 0.06 endotoxin units per ml.
[5]Liposomes composed of phosphatidyl choline: phosphatidyl glycerol 7:3 molar ratio.

EXAMPLE 14
Increased effect of Compound IIA with Lipopolysaccharide In-Vivo

BALB/C mice 7–8 weeks of age were injected subcutaneously with Meth A sarcoma (1×10$^6$ cells) and treated intravenously on day 8 with 10 μg of lipopolysaccharide (LPS) from *Salmonella typhimurium* ReG 30/21 alone or combined with 1 or 10 μg of MDP or Compound IIA. Tumor growth was compared on day 6 following therapy.

The animals were followed and the percent cured determined at 60 days post-injection.

The results noted in Table 3 indicate synergistic activity of compound IIA and LPS.

TABLE 3

| EFFECT OF COMPOUND IIA WITH LIPOPOLYSACCHARIDE ON GROWTH OF TUMORS IN MICE | | |
|---|---|---|
| Group[1] | Percent Change in Average Tumor Area 6 Days Post Treatment | Complete Regression at Day 60 |
| Control | 191% | 0% |
| LPS$_{10}$ | 165% | 0% |
| LPS$_{10}$MDP$_{1.0}$ | 22% | 33% |
| LPS$_{10}$Compound IIA$_{1.0}$ | −56% | 50% |
| LPS$_{10}$MDP$_{10}$ | −56% | 75% |
| LPS$_{10}$Compound IIA$_{10}$ | −67% | 100% |

[1]The subscripts refer to the weight in micrograins.

EXAMPLE 15
Acute Toxicity in Mice and Guinea Pigs

Two mice weighing between 17 and 22 grams and two guinea pigs weighing less than 400 grams were given a single intraperitoneal injection of 0.5 ml and 5.0 ml of a final clinical formulation consisting of a total of 1 mg of Compound IIA, 175 mg of 1-palmitoyl-2-oleoyl phosphatidyl choline and 75 mg of dioleoyl phosphatidyl glycerol per 5 ml. The animals were observed daily for weight and clinical signs of distress. The results showed an initial weight loss followed by a weight gain at 7 days in guinea pigs. Mice maintain their weight and showed a gain at 7 days.

EXAMPLE 16
Subacute Toxicity in Mice

A group of 10 mice were injected intravenously twice a week for four weeks with a dose of 1,320 μg of compound IIA per Kg of body weight. This is calculated to be equivalent to ten times an anticipated maximum human dose of 4 mg per meter squared. In the conversion from a meter squared to a kilogram basis an equivalency of 60 kilograms per 1.73 meter squared body surface area was used instead of the usual equivalency of 70 Kg body mass for a 1.73 meter squared body surface area to result in a somewhat higher dose for the toxicity studies. The results showed no weight loss over the four weeks of the test.

EXAMPLE 17
Subacute Toxicity in Rabbits

Three rabbits were treated intravenously, daily for 14 days at a dose of 132 μg of Compound IIA in liposomes per kilogram of body weight. Blood obtained by cardiac puncture for clinical studies and complete autopsies for histological evidence of toxicity were performed on day 15. Blood was obtained by ear vein and by cardiac puncture on three control rabbits.

The results of this study showed no pathological evidence of toxicity. Review of the blood chemistries from the treated rabbits in comparison to the controls revealed a single rabbit with a significant increase in the creatinine phosphokinase. This abnormal value is believed related to the trauma of the cardiac puncture as evidenced by the increase in the creatinine phosphokinase in the control animals following cardiac puncture.

PREPARATION OF GlcNAcMurNAc-L-Ala-D-isoGln-D-Ala-DpG (IIB)

EXAMPLE 18
BOC-D-Ala-DPG

BOC-D-Ala-DPG was prepared from BOC-D-alanine (Sigma) using the same procedure described for the L-isomer in Example 1. Following workup and drying, the product was obtained as a white amorphous solid in an 89% yield.

EXAMPLE 19
D-Ala-DPG

A portion (657 mg) of BOC-D-Ala-DPG was deprotected with TFA following the procedure described in Example 2. Following workup and drying under high vacuum, 650 mg of product was obtained as its trifluoroacetate salt.

EXAMPLE 20
GlcNAcMurNAc-L-Ala-D-isoGln-D-Ala-DpG (IIB)

GlcNAcMurNAc-L-Ala-D-isoGln-D-Ala-DpG was prepared from GlcNAcMurNAc-L-Ala-D-isoGln (see Example 7) and D-AlaDPG following the same procedure described in Example 8 for the L-isomer. The reaction was followed by TLC and stopped at 72 hours. The reaction mixture was then concentrated to dryness on the rotary evaporator, then further dried under high vacuum to yield the crude product as a yellow solid. This material was extracted three times by suspension in 15 ml-portions of EtOAc followed by centrifugation. The pellet was taken up in ca. 20 ml of $H_2O$, then dialyzed (Spectrapor 7, 2000 MWCO) three times against 1000 ml of $H_2O$. The inner dialysate was then lyophilized to yield 111 mg of product as a white electrostatic solid.

For further purification, a 99 mg-sample of the above product was dissolved in 1.0 ml of $CHCl_3$:MeOH:$H_2O$ (2:3:1), then applied to a 1×28 cm column of Sephadex LH-20 resin that had been packed in the same solvent. The column was eluted with solvent at a flow rate of 0.5 ml/min and fractions of ca. 2.0 ml were collected and analyzed by TLC (see Example 6). The appropriate fractions were combined, then applied directly to a 1×7 cm column of BioRad Cellex D resin (acetate form) that had been packed in the same solvent used above for the LH-20 chromatography. The column was washed with 50 ml of solvent, and the combined eluate and washings concentrated to near dryness on the rotary evaporator, treated with sterile H$_2$O (50 ml), then lyophilized to yield pure product as a white electrostatic solid. Molecular Weight (HRMS): (Molecular Ion+H)$^+$ Calc: 1317.8272; Found: 1317.8274.

PREPARATION OF GlcNAcMurNAc-L-Ala-D-isoGln-L-Ala-NHDPG (IA)

EXAMPLE 21

BOC-L-Ala-SerOH

BOC-L-Ala (567 mg, 2 mMol) and HOBT.H$_2$O (505 mg, 3.3 mMol) were dissolved in 5 ml CH$_2$Cl$_2$ and 5 ml DMF, then treated with 1,3-dicyclohexylcarbodiimide (DCC, 680 mg, 3.3 mMol). The resulting solution was stirred at RT for one hour, then treated dropwise with a solution that contained 421 mg (3.3 mMol) of serinol hydrochloride (Aldrich) and 333 mg (3.3 mMol) of N-methylmorpholine in 5 ml of DMF. The reaction mixture was stirred at RT for 20 hours, then treated with 0.5 ml of glacial acetic acid and stirred for another hour. The solid reaction by-products were removed by filtration and washed with 20 ml CH$_2$Cl$_2$. The combined filtrate and washings was concentrated to dryness on the rotary evaporator then further dried under high vacuum. The oily residue was taken up in 50 ml of H$_2$O, cooled at 4° C. for several hours, then filtered. The filtrate was concentrated to dryness on the rotary evaporator, then further dried under high vacuum to yield the crude product as a yellow oil.

For purification, the entire crude reaction product was dissolved in 25 ml of CHCl$_3$, then applied to a 2.5×20 cm column of BioSil A (100–200 mesh) that had been packed in CHCl$_3$. The column was then successively eluted with (A) 200 ml of CHCl$_3$, (B) 200 ml of 1% (v/v) MeOH in CHCl$_3$, (C) 200 ml of 2% MeOH in CHCl$_3$, (D) 200 ml of 4% MeOH in CHCl$_3$, (E) 200 ml of 6% MeOH in CHCl$_3$, (F) 200 ml of 10% MeOH in CHCl$_3$, and (6) 200 ml of 15% MeOH in CHCl$_3$. Fractions of 50–100 ml were collected and assayed by TLC (Eastman silica; ethyl acetate:pyridine:acetic acid:water, 30:2:0.6:1; HCl spray, then ninhydrin). The appropriate fractions ($R_f$ 0.9) were combined, then concentrated to dryness to yield 739 mg (94%) of product as a white glassy solid.

EXAMPLE 22

BOC-L-Ala-NHDPG

The entire reaction product from Example 21 (739 mg, 2.82 mMol) was dissolved in 50 ml of CH$_2$Cl$_2$, then treated with palmitic acid (1.59 g, 6.2 mMol), DMAP (344 mg, 2.82 mMol) and EDCI (1.19 g, 6.2 mMol). The mixture was stirred at RT for 20 hours, and the reaction was followed by TLC (Eastman silica; hexane:2-propanol, 9:1; HCl spray, then ninhydrin). After removal of the solvent on the rotary evaporator, the resulting oily residue was partitioned between 100 ml of EtOAc and 100 ml of H$_2$O, the layers separated, and the organic layer further washed with H$_2$O (3×50 ml), then concentrated to dryness in the rotary evaporator to yield a colorless oil. This was dissolved in ca. 25 ml of CHCl$_3$:MeOH:H$_2$O (300:200:30), then applied to a 2.5×8 cm column of Whatman DE 52 resin (OH cycle) that had been packed in the same solvent. The column was washed with 500 ml of solvent, the entire eluate collected, then concentrated to dryness on the rotary evaporator to yield an oil that solidified while drying under high vacuum. There was obtained 2.02 g (97%) of crude product as a white amorphous solid.

For further purification, 1.0 g of this product was dissolved in 10 ml of hexane, then applied to a 1.5×28 cm column of BioSil A that had been packed in hexane. The column was then eluted with (A) 50 ml of hexane, (B) 100 ml of 2% (v/v) i-PrOH in hexane, (C) 100 ml of 4% i-PrOH in hexane, and (D) 100 ml of 6% i-PrOH in hexane. Fractions of ca. 20 ml were collected and assayed by TLC as above. The appropriate fractions were combined, concentrated to dryness, then further dried under high vacuum to yield 856 mg of pure product as a white amorphous solid.

EXAMPLE 23

L-Ala-NHDPG 850 mg (1.15 mMol) of the product from Example 22 was dissolved in 15 ml of CH$_2$Cl$_2$, then treated with 10 ml of TFA. After standing at RT for one hour, the solvents were removed on the rotary evaporator to leave a colorless oil that was repeatedly taken up in 10 ml-portions of hexane then concentrated to dryness on the rotary evaporator. After extensive drying under high vacuum, 856 mg (100%) of solid product was obtained as its trifluoroacetate salt.

EXAMPLE 24

GlcNAcMurNAc-L-Ala-D-isoGln-L-Ala-NHDPG (IA)

The disaccharide dipeptide, GlcNAcMurNAc-L-Ala-D-isoGln, (see Example 7, 208.7 mg, 0.3 mMol) and HOBT.H$_2$O (53.3 mg, 0.348 mMol) were dissolved in 10 ml of DMF, then diluted with 7 ml of CH$_2$Cl$_2$. To this was added 66.4 mg (0.346 mMol) of EDCI, and the resulting solution was stirred at RT for 30 minutes.

A TEA solution was prepared by diluting 303 mg (0.42 ml) of TEA to 10 ml with CH$_2$Cl$_2$.

L-Ala-NHDPG (see Example 23, 226.2 mg, 0.3 mMol) was treated with 1.5 ml of CH$_2$Cl$_2$, then with 1.0 ml of the TEA solution. The resulting solution was added to the activated disaccharide dipeptide solution, and the reaction mixture was stirred at RT and the course of the reaction was monitored by TLC (See Example 6). The reaction was stopped after 20 hours, and the reaction mixture was filtered from the small amount of insoluble material, then concentrated to dryness on the rotary evaporator and further dried under high vacuum to yield a yellow semisolid residue. This material was then purified by the procedure described in Example 20 (i.e., EtOAc extraction and dialysis against sterile H$_2$O) to yield 155 mg of a white electrostatic powder. For final purification, a 140 mg-sample was subjected to the same treatment as described in Example 20 (i.e., Sephadex LH-20 and Cellex D). Following the column treatments and lyophilization, the product was obtained as a white electrostatic powder. Molecular Weight (HRMS): (Molecular Ion+H)$^+$ Calc: 1316.8432; Found: 1316.8389.

PREPARATION OF GlcNAcMurNAc-L-Ala-D-isoGln-D-Ala-NHDPG (IB)

EXAMPLE 25

BOC-D-Ala-SerOH

BOC-D-Ala-SerOH was prepared on a 1.0 mMol-scale by the DCC-HOBT mediated condensation of BOC-D-Ala and serinol following the procedure described in Example 21. The crude reaction product was purified by chromatography on a 1.7×24 cm column of BioSil A by successive elution with (A) 100 ml CHCl$_3$, (B) 100 ml of 1% (v/v) MeOH/CHCl$_3$, (C) 100 ml of 2% MeOH/CHCl$_3$, (D) 100 ml of 4% MeOH/CHCl$_3$, (E) 100 ml of 8% MeOH/CHCl$_3$, and (F) 100 ml of 12% MeOH/CHCl$_3$. The appropriate column fractions were combined and concentrated to dryness on the rotary evaporator. The oily residue was then taken up in 10 ml of CH$_2$Cl$_2$, filtered from the small amount of insoluble material, and again concentrated to dryness. The residue was further dried under high vacuum to yield 168 mg (68%) of product as a colorless viscous oil.

EXAMPLE 26
BOC-D-Ala-NHDPG

BOC-D-Ala-NHDPG was prepared on a 0.64 mMol-scale by the EDCI/DMAP mediated condensation of BOC-D-Ala-SerOH and palmitic acid following the procedure described in Example 22. After the coupling reaction and the ensuing workup, the crude product was purified by ion exchange (Cellex D, OH-cycle) and silica gel (BioSil A) chromatography as described in Example 22. The column fractions containing pure product were combined, concentrated to dryness on the rotary evaporator, then further dried under high vacuum to yield 310 mg (65.5%) of product as a white amorphous solid.

EXAMPLE 27
D-Ala-NHDPG 310 mg (0.42 mMol) of the product from Example 26 was dissolved in 10 ml of CH$_2$Cl$_2$, then treated with 5 ml of TFA. After standing at RT for one hour, the reaction was worked up exactly as described in Example 23 for the L-isomer. After extensive drying under high vacuum, there was obtained 315 mg (99.7%) of the trifluoroacetate salt of the product as a white amorphous solid.

EXAMPLE 28
GlcNAcMurNAc-L-Ala-D-isoGln-D-Ala-NHDPG (IB)

The EDCI/HOBT mediated condensation of GlcNAcMurNAc-L-Ala-D-isoGln (see Example 7) with D-Ala-NHDPG (see Example 27) was carried out on a 0.24 mMol-scale following the procedure described in Example 24. Following the coupling reaction and the ensuing workup, the product was purified by the procedure described in Example 20 (i.e., EtOAc extraction and dialysis against distilled water) to yield, after lyophilization, 141 mg of a white powder.

For final purification, a 125 mg-sample of the above product was subjected to the two column procedure (i.e., Sephadex LH-20 and Cellex D) described in Example 20. After lyophilization, the pure product was obtained as a white, electrostatic powder. Molecular Weight (HRMS): (Molecular Ion +H)+Calc: 1316.8432; Found: 1316.8375.

PREPARATION OF GlcNAcMurNAc-D-Ala-D-isoGln-D-Ala-NHDPG (IC)

EXAMPLE 29
GlcNAcMurNAc-D-Ala-D-isoGln-OBn

GlcNAcMurNAc-D-Ala-D-isoGln-OBn was prepared on a 0.75 mMol-scale by the Woodward's Reagent K-mediated coupling of GlcNAcMurNAc (VII) with D-Ala-D-isoGln-OBn (prepared as described in Example 4 and 5) using the procedure in Example 6. Following the 72 hour-coupling reaction and the ensuing workup and lyophilization, 332 mg of product was obtained as a white powder.

EXAMPLE 30
GlcNAcMurNAc-D-Ala-D-isoGln

The entire reaction product from Example 29 (332 mg, 0.423 mMol) was deprotected by hydrogenation over a Pd/C catalyst using the procedure described in Example 7. Following workup and lyophilization, 313.1 mg of product was obtained as a glassy solid.

EXAMPLE 31
GlcNAcMurNAc-D-Ala-D-isoGln-D-Ala-NHDPG (IC)

The EDCI/HOBT mediated condensation of GlcNAcMurNAc-D-Ala-D-isoGln (see Example 30) with D-Ala-NHDPG (see Example 27) was carried out on a 0.25 mMol-scale following the procedure detailed in Example 24. Following the coupling reaction and the ensuing workup, the product was purified by the procedure described in Example 20 (i.e., EtOAc extraction and dialysis against distilled water) to yield, after lyophilization, 102 mg of a white powder.

For final purification, a 90 mg-sample of the above product was subjected to the two column procedure (i.e., Sephadex LH-20 and Cellex D) described in Example 20. After lyophilization, the pure product was obtained as a white, electrostatic powder. Molecular Weight (HRMS): (Molecular Ion+H)+ Calc: 1316.8432; Found: 1316.8444.

PREPARATION OF GlcNAcMurNAc-D-Ala-D-isoGln-D-Ala-DPG (IIC)

EXAMPLE 32
GlcNAcMurNAc-D-Ala-D-isoGlu-D-Ala-DPG (IIC)

The EDCI/HOBT mediated condensation of GlcNAc MurNAc-D-Ala-D-isoGln (see Example 30) with D-Ala-DPG (see Examples 18 and 19) was carried out as described in Examples 8 and 20. After the 72 hour-incubation, the reaction mixture was worked up as described in Example 20, i.e., by EtOAc extraction and extensive dialysis against distilled H$_2$O. The crude lyophilized product was then further purified by the described two-column approach (i.e., Sephadex LH-20 followed by BioRad Cellex D [acetate form]). After removal of the organic solvents, the column eluate was lyophilized to yield Compound IIC as a white electrostatic powder.

EXAMPLE 33

Activation of Monocytes In-Vitro by Drug Compounds as Measured by the Production of Tumor Necrosis Factor Human peripheral blood monocytes were isolated by density gradient centrifugation as noted in Example 13. The cell number was adjusted to $5 \times 10^5$ cells per ml in RPM 1640 media containing 5% human AB negative serum. One ml containing $5 \times 10^5$ cells were placed in individual wells of a 24-well Plastek tissue culture plate. Various drugs in a volume of 0.5 ml were added at time zero. The cells were incubated at 37° C. in a 5% CO$_2$ atmosphere. Aliquots (0.1 ml) of the supernatant were removed at 24 hours and frozen at −80° C. These samples were subsequently assayed for tumor necrosis factor (TNF) activity using a commercially available ELISA Assay from T-Cell Sciences (Cambridge, Mass.). The results of a series of four similar experiments, set forth in Table 4, demonstrate significant levels of TNF production by all compounds as compared to a control.

TABLE 4

| | TNF Production by Monocytes Incubated with Compounds Suspended in Saline. | | |
|---|---|---|---|
| Experiment | Drug Compound | Concentration of Free Drug (µg/ml) | TNF Level (pg/ml) |
| 1 | 1. Control | — | 500 |
| | 2. Compound IIA | 0.1 | 1760 |
| | | 1.0 | 1600 |
| | | 10.0 | 4550 |
| 2 | 1. Control | — | 170 |
| | 2. Compound IIA | 0.1 | 1450 |

TABLE 4-continued

TNF Production by Monocytes Incubated with Compounds Suspended in Saline.

| Experiment | Drug Compound | Concentration of Free Drug (µg/ml) | TNF Level (pg/ml) |
|---|---|---|---|
| | | 1.0 | 1580 |
| | | 10.0 | 1630 |
| | 3. MDP | 0.1 | 1450 |
| | | 1.0 | 1200 |
| | | 10.0 | 800 |
| 3 | 1. Control | — | 130 |
| | 2. Compound IIA | 0.1 | 1450 |
| | | 1.0 | 1650 |
| | | 10.0 | 1800 |
| | 3. Compound IIB | 0.1 | 250 |
| | | 1.0 | 500 |
| | | 10.0 | 1600 |
| | 4. Compound IA | 0.1 | 280 |
| | | 1.0 | 1000 |
| | | 10.0 | 1680 |
| | 5. Compound IB | 0.1 | 180 |
| | | 1.0 | 350 |
| | | 10.0 | 1980 |
| | 6. Compound IC | 0.1 | 280 |
| | | 1.0 | 300 |
| | | 10.0 | 250 |
| 4 | 7. Control | — | 50 |
| | 8. Compound IIC | 0.1 | 40 |
| | | 1.0 | 110 |
| | | 10.0 | 450 |

EXAMPLE 34
Activation of Monocytes In-Vitro by Drug Compound Incorporated in Liposomes Human peripheral blood monocytes were isolated by density gradient centrifugation as described in Example 13. The cells were plated in 24-well microliter plates as described in Example 33. The compounds were prepared in liposomes as described in Example 10, and assayed for TNF production, as described in Example 33. The results are set forth in Table 5, and show significant levels of TNF compared to controls.

TABLE 5

TNF Production by Monocytes Incubated with Compounds Incorporated in Liposomes

| Drug Compound | Concentration of Drug (µg/ml) | TNF Level (pg/ml) |
|---|---|---|
| Control | — | 70 |
| Compound IIA | 0.1 | 1270 |
| | 1.0 | 850 |
| | 10.0 | 1050 |
| Compound IA | 0.1 | 430 |
| | 1.0 | 800 |
| | 10.0 | 750 |

EXAMPLE 35
Activation of Monocytes In-Vitro as Measured by In-Vitro Tumor Cell Cytotoxicity Human peripheral blood mononuclear cells were isolated by density gradient centrifugation on 46% Percoll. $1 \times 10^5$ of the mononuclear cells were plated onto Falcon microliter plates and allowed to adhere for two hours. The non-adherent cells were removed and fresh media added. The cells were allowed to incubate for 24 hours after which various concentrations of the drug either alone or incorporated in liposomes was added. After 24 hours, the plates were washed and $1 \times 10^4$ $I^{125}$ labelled target cells were added. Following an additional 72 hours of coincubation, the plates were washed and the residual radioactivity determined. The specific cytotoxicity was calculated from the formula:

$$\% \text{ cytotoxicity} = \frac{A - B}{A} \times 100$$

The results of cytotoxicity assay of various compounds alone or incorporated in liposomes at various concentrations is given in Table 6. All of the tested compounds, either alone or incorporated in liposomes, demonstrated ability to activate monocytes to be cytotoxic.

TABLE 6

In-Vitro Cytotoxicity of Various Compounds and Formulations

| Compound | Formulation | Concentration (µg/ml) | Cytotoxicity (%) |
|---|---|---|---|
| Control | | | 1.4 |
| Compound IA | PC/PG[1] | 0.1 | 7.0 |
| | | 1.0 | 7.0 |
| | | 10.0 | 6.0 |
| Compound IC | PC/PG[1] | 0.1 | 10.0 |
| | | 1.0 | 4.0 |
| | | 10.0 | 12.0 |
| Compound IIA | PC/PS[2] | 0.1 | 1.0 |
| | | 1.0 | 8.0 |
| | | 10.0 | 12.0 |
| Compound IA | PC/PS[2] | 0.1 | 8.0 |
| | | 1.0 | 5.0 |
| | | 10.0 | 19.0 |
| Compound IC | | 0.1 | 5.0 |
| | | 1.0 | 16.0 |
| | | 10.0 | 15.0 |
| Compound IIA | | 0.1 | 5.0 |
| | | 1.0 | 4.0 |
| | | 10.0 | 3.0 |
| Compound IA | | 0.1 | 1.0 |
| | | 1.0 | 4.0 |
| | | 10.0 | 3.0 |
| MDP | | 0.1 | 11.0 |
| | | 1.0 | 9.0 |
| | | 10.0 | 7.0 |

[1] PC/PG: phosphatidyl choline/phosphatidyl glycerol liposomes (7:3 molar ratio)
[2] PC/PS: phosphatidyl choline/phosphatidyl serine liposomes (7:3 molar ratio)

PREPARATION OF GlcNAcMurNAc-F-Thr-D-isoGln-F-Ala-DpG (IID)

EXAMPLE 36
BOC-D-isoGln-OBn

Benzyl alcohol (476 mg, 4.4 mMol) BOC-D-isoGln (Sigma, 985.2 mg, 4.0 mMol) and DMAP (244 mg, 2.0 mMol) were dissolved in 30 ml $CH_2Cl_2$ and 20 ml DMF, then treated with EDCI (920 mg, 4.8 mMol), and the resulting solution stirred at RT for 24 hours. The reaction mixture was then concentrated to dryness on a rotary evaporator to yield an oily residue that was partitioned between 75 ml EtOAc and 25 ml $H_2O$. The layers were separated and the organic layer extracted with saturated $NaHCO_3$ (3×25 ml) and $H_2O$ (3×25 ml). After drying over $Na_2SO_4$, the solvent was removed on the rotary evaporator to yield 1,206 g (90%) of a white solid, which was further purified by crystallization from diethyl ether/hexane to yield pure product as a snow-white solid.

EXAMPLE 37
D-isoGln-OBn

A sample (1.0 g, 2.98 mMol) of the product from Example 36 was dissolved in 50 ml of 1N HCl/HOAc and the resulting solution allowed to stand at RT for two hours. The solvent was then removed on the rotary evaporator to yield a white solid that was further dried under high vacuum, then crystallized from MeOH/ether to yield 720 mg (90%) of the pure product as its hydrochloride salt.

EXAMPLE 38
BOC-F-Thr(OBn)-D-isoGln-OBn

BOC-L-Thr(OBn) (Sigma, 618.8 mg, 2.0 mMol), and N-hydroxysuccinimide (253.2 mg, 2.2 mMol) were dissolved in 5.0 ml DMF and 7.0 ml CH$_2$Cl$_2$. To this was added EDCI (421.7 mg, 2.2 mMol), and the resulting solution stirred at RT for one hour. Then, a solution that contained 440.4 mg (1.62 mMol) of the product from Example 37 and 164 mg (1.62 mMol) of N-methylmorpholine in 5.0 ml DMF was added and the reaction mixture was stirred at RT for 48 hours. The solvents were then removed on the rotary evaporator to yield an oily residue that was partitioned between 100 ml EtOAc and 50 ml H$_2$O. The layers were separated, and the organic layer further extracted with saturated NaHCO$_3$ (3×50 ml), then H$_2$O (3×50 ml). The organic layer was concentrated to dryness on the rotary evaporator, then further dried under high vacuum to yield crude product as a yellow glassy solid.

For further purification, the entire product was dissolved in 10 ml CHCl$_3$, then applied to a 2.5×18 cm column of BioSil A that had been packed in CHCl$_3$. The column was then successively eluted with (A) 200 ml CHCl$_3$, (B) 200 ml of 1% MeOH/CHCl$_3$, (C) 200 ml of 2% MeOH/CHCl$_3$, and (D) 200 ml of 3% MeOH/CHCl$_3$. Fractions of ca. 20 ml were collected, and aliquots (2 ul) of each were assayed by TLC as described in Example 21. The appropriate fractions were combined, concentrated to dryness, then further dried under high vacuum to yield product as a white glassy solid.

For final purification, the entire product was crystallized from EtOAc/hexane to yield, after drying, 550 mg (65% overall) of pure product as a white glassy solid.

EXAMPLE 39
L-Thr(OBn)-D-isoGln-OBn

The product from Example 38 (540 mg, 1.044 mMol) was dissolved in 50 ml of 1N HCl/HOAc and the resulting solution stirred at RT for 1.5 hours. After removal of solvent on the rotary evaporator, the oily residue was further dried under high vacuum, then crystallized from MeOH/ether to yield, after extensive drying, 450mg of the hydrochloride salt of L-Thr(OBn)-D-isoGln-OBn as a white, amorphous solid.

EXAMPLE 40
GlcNAcMurNAc-F-Thr(OBn),D,isoGln-OBn

GlcNAcMurNAc-L-Thr(OBn)-L-isoGln-OBn was prepared on a 0.60 mMol-scale by the Woodward's Reagent K-mediated coupling of GlcNAcMurNAc (VII) with the product from Example 39 using the procedure described in Example 6. Following the 96 hour-coupling reaction and the ensuing workup and lyophilization, 388 mg of product was obtained as a white powder.

EXAMPLE 41
GlcNAcMurNAc-F-Thr-D-isoGln 263 mg of the product from Example 40 was dissolved in 75 ml of 10% HOAc, then deprotected by hydrogenation over a Pd/C catalyst using the procedure described in Example 7. Following workup and lyophilization, 201 mg of product was obtained as a glassy tan solid.

EXAMPLE 42
GlcNAcMurNAc-F-Thr-D-isoGln-F-Ala-DPG (IID)

The EDCI/HOBT mediated condensation of GlcNAcMurNAc-L-Thr-D-isoGln (see Example 41) with L-Ala-DPG (see Example 2) was carried out on a 0.10 mMol-scale following the procedures described in Examples 8 and 20. After the 48 hour-incubation, the reaction mixture was worked up as described in Example 20, i.e., by EtOAc extraction and extensive dialysis against distilled H$_2$O. The crude lyophilized product was then purified by the described two-column approach, i.e., Sephadex LH-20 followed by BioRad Cellex D (acetate form). After removal of the organic solvents, the final column eluate was lyophilized to yield pure product as a white electrostatic powder.

PREPARATION OF GlcNAcMurNAc-F-Thr-D-isoGln-F-Ala-NHDPG (ID)

EXAMPLE 43
GlcNAcMurNAc-F-Thr-D-isoGln-F-Ala-NHDPG (ID)

The EDCI/HOBT mediated condensation of GlcNAcMurNAc-L-Thr-D-isoGln (see Example 40) with L-Ala-NHDPG (see Example 23) was carried out on a 0.1 mMol-scale following the procedure detailed in Example 24. After the 48 hour-coupling reaction, the reaction mixture was worked up, then purified as described in Example 24. The final column eluate was lyophilized to yield pure product as a white electrostatic powder.

PREPARATION OF GlcNAcMurNAc-F-Ser-D-isoGln-F-Ala-DPG (IIE)

EXAMPLE 44
BOC-F-Ser(OBn)-D-isoGln-OBn

This compound was prepared on a 1.0 mMol-scale using the same procedure described in Example 38 for the synthesis of the threonine analog. After workup and purification by both silica gel (BioSil A) chromatography and crystallization from EtOAc/hexane, pure product was obtained in a 79% yield as a white, amorphous solid.

EXAMPLE 45
L-Ser(OBn)-D-isoGln-OBn

The product from Example 44 (300 mg, 0.6 mMoL) was treated with 30 ml of 1N HCl/HOAc, and the resulting solution was allowed to stand at RT for 2 hours. After removal of the solvent on the rotary evaporator, the oily residue was further dried under high vacuum, then crystallized form MeOH/ether (see Example 5) to yield, after extensive drying, 234 mg of the hydrochloride salt of L-Ser(OBn)-D-isoGln-OBn as a white, amorphous solid.

EXAMPLE 46
GlcNAcMurNAc-F-Ser(OBn)-D-isoGln-OBn

GlcNAcMurNAc-L-Ser(OBn)-D-isoGln-OBn was prepared on a 0.20 mMol-scale by the Woodward's Reagent K-mediated coupling of GlcNAcMurNAc (VII) with the product from Example 45 using the procedure described in Example 6. Following the 120 hour-coupling reaction and the ensuing workup and lyophilization, 110 mg of product was obtained as a white powder.

EXAMPLE 47
GlcNAcMurNAc-F-Ser-D-isoGln 108 mg of the product from Example 46 was dissolved in 50 ml of 10% HOAc, then deprotected by hydrogenation over a Pd/C catalyst using the procedure described in Example 7. Following workup and lyophilization, 95 mg of the crude product was obtained as a white glassy solid.

For further purification, the entire 95 mg of product was slurried in 2.0 ml of CHCl$_3$, then treated with sufficient MeOH to effect solution. This was then applied to a 0.7×28 cm column of BioSil A that had been packed in CHCl$_3$. The column was then successively eluted with (A) 50 ml of CHCl$_3$, (B) 50 ml of 20% MeOH/CHCl$_3$, (C) 100 ml of 40% MeOH/CHCl$_3$, (D) 100 ml of 60% MeOH/CHCl$_3$, and (E) 100 ml of 80% MeOH/CHCl$_3$. Fractions of ca. 5.0 ml were collected and aliquots (2λ) of each were assayed by TLC (see Example 6). The tubes containing material with $R_f$ 0.0 were combined, concentrated to dryness, then redissolved in 10 ml of H$_2$O and lyophilized to yield pure product as a white, electrostatic solid.

EXAMPLE 48
GlcNAcMurNAc-F-Ser-D-isoGln-F-Ala-DPG (IIE)

The EDCI/HOBT mediated condensation of GlcNAcMurNAc-L-Ser-D-isoGln (see Example 47) with L-Ala-DPG (see Example 2) was carried out on a 0.045 mMol-scale following the procedures described in Examples 8 and 20. After the 48 hour-reaction, the mixture was worked up as described in Example 20, i.e., by EtOAc extraction and extensive dialysis against distilled water. The crude lyophilized product was then purified by the described two column approach (i.e., Sephadex LH-20 followed by BioRad Cellex D (acetate form)). After removal of the organic solvents, the final column eluate was lyophilized to yield pure product as a white, electrostatic powder.

PREPARATION OF GlcNAcMurNAc-F-Val-D-isoGln-F-Ala-DPG (IIF)

EXAMPLE 49
BOC-F-Val-D-isoGln-OBn

BOC-L-Val-D-isoGln-OBn was prepared on a 1.0 mMol-scale using the same procedure described in Example 38 for the synthesis of the threonine analog. After workup and purification by both silica gel (BioSil A) chromatography and crystallization from the EtOAc/hexane, pure product was obtained in a 60% yield as a white, amorphous solid.

EXAMPLE 50
L-Val-D-isoGln-OBn

The product from Example 49 (175 mg, 0.40 mMol) was treated with 20 ml of 1N HCl/HOAc, and the resulting solution was allowed to stand at RT for 2 hours. After removal of the solvent on a rotary evaporator, the oily residue was further dried under high vacuum, then crystallized from MeOH/ether (see Example 5) to yield, after thorough drying, 134 mg of the hydrochloride salt of L-Val-D-isoGln-OBn as a white, amorphous solid.

EXAMPLE 51
GlcNAcMurNAc-F-Val-D-isoGln-OBn

GlcNAcMurNAc-L-Val-D-isoGln-OBn was prepared on a 0.20 mMol-scale by the Woodward's Reagent K-mediated coupling of GlcNAcMurNAc (VII) with the product from Example 50 using the procedure detailed in Example 6. Following the 96 hour-coupling reaction and the ensuing workup and lyophilization, 95 mg of product was obtained as a white powder.

EXAMPLE 52
GlcNAcMurNAc-F-Val-D-isoGln 95 mg of the product from Example 51 was dissolved in 50 ml of the 10% HOAc, then deprotected by hydrogenation over a Pd/C catalyst using the procedure described in Example 7. Following workup and lyophilization, 87 mg of the crude product was obtained as a white glassy solid. This material was then purified by chromatography on a silica gel column exactly as described in Example 47. Fractions containing material with $R_f$ 0.05 were combined, concentrated to dryness, then redissolved in 10 ml of H$_2$O and lyophilized to yield pure product as a white powder.

EXAMPLE 53
GlcNAcMurNAc-F-Val-D-isoGln-F-Ala-DpG (IIF)

The EDCI/HOBT mediated condensation of GlcNAcMurNAc-L-Val-D-isoGln (see Example 52) with L-Ala-DPG (see Example 2) was carried out on a 0.048 mMol-scale following the procedures detailed in Examples 8 and 20. After the 48 hour-coupling reaction, the mixture was worked up exactly as described in Example 20, i.e., by EtOAc extraction followed by extensive dialysis against distilled water. The crude lyophilized product was then purified by the described two column approach and lyophilized to yield pure product as a white electrostatic powder.

PREPARATION OF GlcNAcMurNAc-F-Ala-D-isoGln-F-Val-DpG (IIG)

EXAMPLE 54
BOC-F-Val-DPG

BOC-L-Val-DPG was prepared on a 1.0 mMol-scale by the EDCI/DMAP condensation of BOC-L-Val (Sigma) with 1,2-dipalmitoyl-sn-glycerol using the procedure detailed in Example 1 for the preparation of BOC-L-Ala-DPG. Following workup and extensive drying under high vacuum, there was obtained 703 mg (91.5%) of product as an amorphous white solid.

EXAMPLE 55
L-Val-DPG

The product from Example 54 (500 mg) was deprotected with TFA/CH$_2$Cl$_2$ following the procedure described in Example 2. After workup and extensive drying under high vacuum, there was obtained 485 mg of L-Val-DPG trifluoroacetate as an amorphous white solid.

EXAMPLE 56
GlcNAcMurNAc-F-Ala-D-isoGln-F-Val-DpG

The EDCI/HOBT mediated condensation of GlcNAcMurNAc-L-Ala-D-isoGln (see Example 7) with L-Val-DPG (see Example 55) was carried out on a 0.033 mMol-scale following the procedures detailed in Examples 8 and 20. Following the 24 hour-coupling reaction, the mixture was worked up as described in Example 20, i.e., by EtOAc extraction followed by extensive dialysis against distilled water. The crude product was then purified by the described two column approach and lyophilized to yield pure product as a white electrostatic powder.

EXAMPLE 57
Activation of Monocytes In-Vitro by Drug Compounds Formulations as Measured by the Production of Interleukin-1-beta and/or TNF Human peripheral blood monocytes were isolated by density gradient centrifugation as noted in Example 13. The cell number was adjusted to $5 \times 10^5$ cells per ml in RPM 1640 media containing 5% human AB negative serum. One ml containing $5 \times 10^5$ cells were placed in individual wells of 24-well Plastek tissue culture plate. Various drugs in a volume of 0.5 ml were added at time zero. The compounds were also formulated in liposomes as described in Example 10, and added in a volume of 0.5 ml to individual wells of a 24-well Plastek tissue culture plate. The cells were incubated at 37° C. in a 5% CO$_2$ atmosphere. Aliquots (0.1 ml) of the supernatant were removed at 24 hours and frozen at $-20°$ C. These samples were subsequently assayed for TNF as described in Example 33 and Interleukin-1-beta (IL-1β) using a commercially available ELISA kit from Cistron (Pine Brook, N.J.).

The results of a series of two separate experiments set forth in Tables 7, 8, and 9 demonstrate significant levels of IL-1β and/or TNF production by all compounds and formulations of the invention as compared to controls.

TABLE 7

(Experiment 1)
TNF Level (pg/ml) at 24 Hours
Following Incubation of Monocytes with Various Compounds and Formulations

| Compound | TNF (pg/ml) at given Concentration of Compound (μg/ml) | | | |
|---|---|---|---|---|
| | 0.01 | 0.1 | 1.0 | 10.0 |
| IIA | 650 | 460 | 620 | 500 |
| GlcNAcMurNAc—L-Ala—D-isoGln—L-Ala—DPG | | | | |
| IIA in Liposomes | 850 | 670 | 600 | 500 |
| ID | | 0 | 250 | 1060 |
| GlcNAcMurNAc—L-Thr—D-isoGln—L-Ala—NHDPG | | | | |
| ID in Liposomes | 10 | 280 | 180 | 220 |
| IID | 70 | 320 | 1080 | 2150 |
| GlcNAcMurNAc—L-Thr—D-isoGln—L-Ala—DPG | | | | |
| IID in Liposomes | 400 | 400 | 820 | 1400 |
| IIF | 510 | 440 | 480 | 400 |
| GlcNAcMurNAc—L-Val—D-isoGln—L-Ala—DPG | | | | |
| IIF in Liposomes | 570 | 680 | 420 | 540 |
| MDP | 400 | 430 | 380 | 360 |
| GlcNAcMurNAc—L-Thr—D-isoGln | 200 | 440 | 1050 | 1050 |
| Empty Liposomes | 70 | 60 | 80 | 70 |

TABLE 8

(Experiment 1)
Interleukin-1-beta beta Level (pg/ml) at 24 Hours
Following Incubation of Monocytes with Various Compounds and Formulations

| Compound | IL-1-beta (pg/ml) at given Concentration of Compound (μg/ml) | | | |
|---|---|---|---|---|
| | 0.01 | 0.1 | 1.0 | 10.0 |
| IIA | 260 | 220 | 244 | 264 |
| GlCNAcMurNAc—L-Ala—D-isoGln—L-Ala—DPG | | | | |
| IIA in Liposomes | 170 | 186 | 184 | 254 |
| ID | 10 | 16 | 8 | 90 |
| GlcNAcMurNAc—L-Thr—D-isoGln—L-Ala—NHDPG | | | | |
| ID in Liposomes | 40 | 14 | 40 | 40 |
| IID | 70 | 14 | 170 | 690 |
| GlcNAcMurNAc—L-Thr—D-isoGln—L-Ala—DPG | | | | |
| IID in Liposomes | 100 | 40 | 148 | 360 |
| IIF | 220 | 212 | 260 | 260 |
| GlcNAcMurNAc—L-Val—D-isoGln—L-Ala—DPG | | | | |
| IIF in Liposomes | 160 | 180 | 120 | 224 |
| MDP | 180 | 260 | 226 | 240 |
| GlcNAcMurNac—L-Thr—D-isoGln | 50 | 70 | 230 | 630 |
| Empty Liposomes | 14 | 0 | 4 | 0 |

TABLE 9

(Experiment 2)
TNF Level (pg/ml) at 24 Hours
Following Incubation of Monocytes with Various Compounds and Formulations

| Compound | TNF (pg/ml) at given Concentration of Compound (μg/ml) | | |
|---|---|---|---|
| | 0.1 | 1.0 | 10.0 |
| IIA | 1400 | 1700 | 1070 |
| GlcNAcMurNAc—L-Ala—D-isoGln—L-Ala—DPG | | | |
| IIA in Liposomes | 1250 | 1400 | 1200 |
| IIE | 150 | 800 | 1500 |
| GlcNAcMurNAc—L—Ser—D-isoGln—L-Ala—DPG | | | |
| IIE in Liposomes | 130 | 570 | 940 |
| IIG | 1150 | 1500 | 1400 |
| GlcNAcMurNAc—L-Ala—D-isoGln—L-Val—DPG | | | |
| IIG in Liposomes | 1500 | 1600 | 1600 |
| Empty Liposomes | 80 | 50 | 40 |

The invention has been described with reference to various specific and preferred embodiments and techniques. However, it should be understood that many variations and modifications may be made while remaining within the spirit and scope of the invention.

What is claimed is:
1. A compound of the formula:

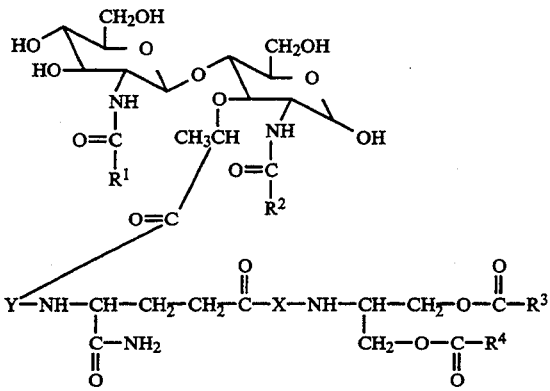

(I)

wherein $R^1$ is $(C_1–C_9)$alkyl, $R^2$ is $(C_1–C_5)$alkyl, $R^3$ and $R^4$ are individually $(C_6–C_{30})$alkyl groups having about 0–4 double bonds, X is a single bond or any peptidyl residue comprising one or more amino acid residues; and Y is any amino acid residue; and the pharmaceutically acceptable salts thereof.

2. The compound of claim 1 wherein $R^1$ is —$CH_3$.

3. The compound of claim 2 wherein $R^2$ is —$CH_3$.

4. The compound of claim 1 wherein X is any amino acid residue.

5. The compound of claim 4 wherein X is any naturally occurring amino acid residue or an enantiomorph of any naturally occurring amino acid residue.

6. The compound of claim 5 wherein X is selected from the group consisting of L-valine, D-valine, L-alanine, and D-alanine.

7. The compound of claim 1 wherein Y is any naturally occurring amino acid residue or an enantiomorph of any naturally occurring amino acid residue.

8. The compound of claim 7 wherein Y is selected from the group consisting of threonine, alanine, valine, and serine.

9. The compound of claim 8 wherein Y is selected from the group consisting of L-alanine and L-threonine.

10. The compound of claim 1 wherein $R^3$ and $R^4$ are individually $(C_{12}–C_{23})$alkyl groups having about 0–1 double bonds.

11. The compound of claim 10 wherein $R^3$ is a $(C_{15})$alkyl group.

12. The compound of claim 11 wherein $R^4$ is a $(C_{15})$alkyl group.

13. The compound of claim 10 wherein $R^1$ and $R^2$ are —$CH_3$.

14. A compound of the formula:

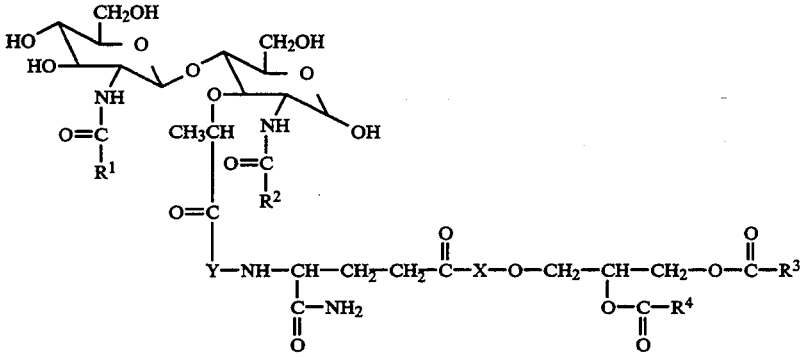

(II)

wherein $R^1$ is $(C_1–C_9)$alkyl, $R^2$ is $(C_1–C_5)$alkyl, $R^3$ and $R^4$ are individually $(C_6–C_{30})$alkyl groups having about 0–4 double bonds, X is a single bond or any peptidyl residue comprising one or more amino acid residues, and Y is any amino acid residue; and the pharmaceutically acceptable salts thereof.

15. The compound of claim 14 wherein $R^1$ is —$CH_3$.

16. The compound of claim 15 wherein $R^2$ is —$CH_3$.

17. The compound of claim 14 wherein X is any amino acid residue.

18. The compound of claim 17 wherein X is any naturally occurring amino acid residue or an enantiomorph of any naturally occurring amino acid residue.

19. The compound of claim 18 wherein X is selected from the group consisting of L-valine, D-valine, L-alanine, and D-alanine.

20. The compound of claim 14 wherein Y is any naturally occurring amino acid residue or an enantiomorph of any naturally occurring amino acid residue.

21. The compound of claim 20 wherein Y is selected from the group consisting of threonine, alanine, valine, and serine.

22. The compound of claim 21 wherein Y is selected from the group consisting of L-alanine and L-threonine residue.

23. The compound of claim 14 wherein $R^3$ and $R^4$ are individually $(C_{12}–C_{23})$alkyl groups having about 0–1 double bonds.

24. The compound of claim 23 wherein $R^3$ is a $(C_{15})$alkyl group.

25. The compound of claim 24 wherein $R^4$ is a $(C_{14})$alkyl group.

26. The compound of claim 23 wherein $R^1$ and $R^2$ are —$CH_3$.

27. A composition of matter comprising an effective immunomodulating amount of the compound of claims 1 and/or 14 combined with a pharmaceutically acceptable liquid vehicle.

28. The composition of claim 27 further comprising a lipopolysaccharide.

29. A liposome comprising a compound of the formula:

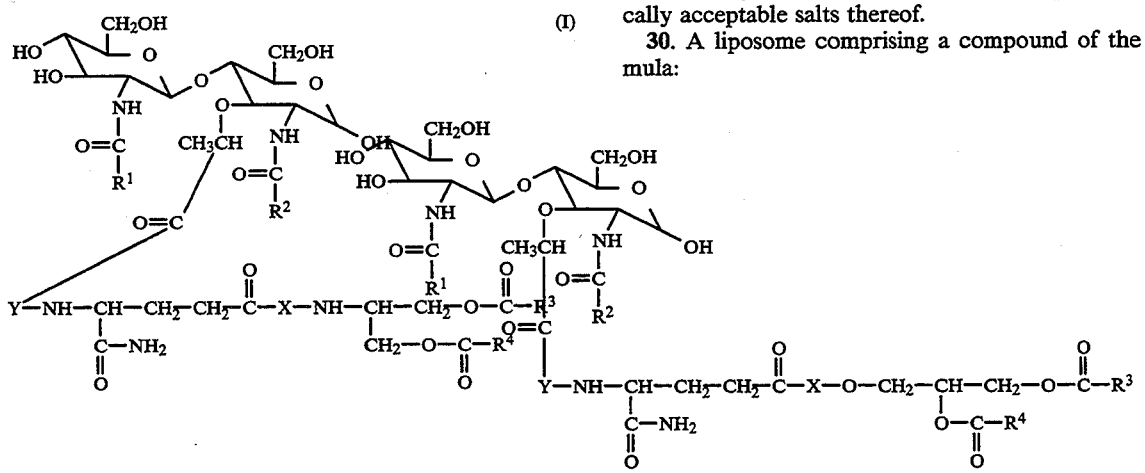

wherein $R^1$ is $(C_1-C_9)$alkyl, $R^2$ is $(C_1-C_5)$alkyl, $R^3$ and $R^4$ are individually $(C_6-C_{30})$alkyl groups having about 0–4 double bonds, X is a single bond or any peptidyl residue comprising one or more amino acid residues, and Y is any amino acid residue; and the pharmaceutically acceptable salts thereof.

30. A liposome comprising a compound of the formula:

(II)

wherein $R^1$ is $(C_1-C_9)$alkyl, $R^2$ is $(C_1-C_5)$alkyl, $R^3$ and $R^4$ are individually $(C_6-C_{30})$alkyl groups having about 0–4 double bonds, X is a single bond or any peptidyl residue comprising one or more amino acid residues, and Y is any amino acid residue; and the pharmaceutically acceptable salts thereof.

31. A composition of matter wherein the liposome consists essentially of a liposome having a bilayer membrane consisting essentially of 1-palmitoyl-2-oleoyl-phosphatidyl choline and dioleoyl phosphatidyl glycerol in a weight ratio of about 5:1 to 1:1 and a compound of claims 1 and/or 14.

32. The composition of claim 31 wherein the weight ratio is about 7:3.

33. A method for stimulating the immune response of a mammal comprising administering an effective amount of the composition of claims 1, 14, 29, 30, or 31; itself or in combination with a pharmaceutically acceptable vehicle.

* * * * *